(12) United States Patent
Oral et al.

(10) Patent No.: US 10,953,136 B2
(45) Date of Patent: Mar. 23, 2021

(54) SYSTEMS AND METHODS OF RADIOPROTECTION OF ALLOGRAFTS

(71) Applicant: The General Hospital Corporation, Boston, MA (US)

(72) Inventors: Ebru Oral, Newton, MA (US); Jeremy Suhardi, Boston, MA (US); Orhun Muratoglu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 16/093,540

(22) PCT Filed: Apr. 17, 2017

(86) PCT No.: PCT/US2017/027861
§ 371 (c)(1),
(2) Date: Oct. 12, 2018

(87) PCT Pub. No.: WO2017/181164
PCT Pub. Date: Oct. 19, 2017

(65) Prior Publication Data
US 2019/0167852 A1 Jun. 6, 2019

Related U.S. Application Data

(60) Provisional application No. 62/323,009, filed on Apr. 15, 2016.

(51) Int. Cl.
*A61L 27/54* (2006.01)
*A61K 35/32* (2015.01)
(Continued)

(52) U.S. Cl.
CPC .............. *A61L 27/54* (2013.01); *A61K 35/32* (2013.01); *A61L 27/3608* (2013.01);
(Continued)

(58) Field of Classification Search
None
See application file for complete search history.

(56) References Cited

U.S. PATENT DOCUMENTS 5,827,904 A 10/1998 Hahn
6,448,315 B1 9/2002 Lidgren et al.
(Continued)

FOREIGN PATENT DOCUMENTS

WO WO-2010016942 A1 * 2/2010 ............. A61L 27/38
WO WO-2013170005 A1 * 11/2013 ............. C08J 7/123

OTHER PUBLICATIONS

Campbell, et al., Sterilization of HIV with Irradiation: Relevance to Infected Bone Allografts, Australian and New Zealand Journal of Surgery, 1999, 69(7):517-521.
(Continued)

*Primary Examiner* — Melissa S Mercier
(74) *Attorney, Agent, or Firm* — Quarles & Brady LLP

(57) ABSTRACT

Systems and methods of protecting allograft against radiation damage are disclosed. Systems and methods of incorporating additives such as radioprotectants into allograft tissue are also disclosed. The systems and methods comprise providing an allograft; cleaning the allograft; contacting the allograft with at least one radioprotectant, thereby obtaining a radioprotectant-doped allograft; contacting the radioprotectant-doped allograft with a supercritical fluid, thereby obtaining a radioprotectant doped and homogenized allograft.

37 Claims, 15 Drawing Sheets

(51) Int. Cl.
　　　*A61L 27/36*　　　(2006.01)
　　　*A61L 27/38*　　　(2006.01)

(52) U.S. Cl.
　　　CPC ....... *A61L 27/3683* (2013.01); *A61L 27/3687* (2013.01); *A61L 27/3691* (2013.01); *A61L 27/3821* (2013.01); *A61L 2300/428* (2013.01); *A61L 2430/02* (2013.01)

(56) References Cited

U.S. PATENT DOCUMENTS

| | | |
|---|---|---|
| 2009/0099663 A1 | 4/2009 | Romagnoli |
| 2012/0213837 A1 | 8/2012 | Botchwey, III |
| 2013/0101675 A1 | 4/2013 | Duneas et al. |
| 2015/0151866 A1 | 6/2015 | Oral et al. |
| 2016/0231056 A1* | 8/2016 | Wei .................. A21C 9/083 |

OTHER PUBLICATIONS

Dane, et al., Nano-Sized Drug-Loaded Micelles Deliver Payload to Lymph Node Immune Cells and Prolong Allograft Survival, Journal of Controlled Release, 2011, 156:154-160.

Delloye, et al., Pelvic Reconstruction with a Structural Pelvic Allograft After Resection of a Malignant Bone Tumor, Journal of Bone and Joint Surgery, 2007, 89(3):579-587.

Itou, et al., Cystathionine γ-lyase Accelerates Osteoclast Differentiation: Identification of a Novel Regulator of Osteoclastogenesis by Proteomic Analysis, Arteriosclerosis, Thrombosis, and Vascular Biology, 2014, 34(3):626-634.

Kattaya, et al., Radioprotectant and Radiosensitizer Effects on Sterility of γ-irradiated Bone, Clinical Orthopaedics and Related Research, 2008, 466(8):1796-1803.

Lietman, et al., Complications of Irradiated Allografts in Orthopaedic Tumor Surgery, Clinical Orthopaedics and Related Research, 2000, 375:214-217.

Lord, et al., Infection in Bone Allografts. Incidence, Nature and Treatment, Journal of Bone & Joint Surgery, 1988, 70-A(3):369-376.

Mikhael, et al., Mechanical Strength of Bone Allografts Subjected to Chemical Sterilization and Other Terminal Processing Methods, Journal of Biomechanics, 2008, 41(13):2816-2820.

Nguyen, et al., Sterilization of Allograft Bone: Effects of Gamma Irradiation on Allograft Biology and Biomechanics, Cell Tissue Banking, 2007, 8:93-105.

Quarles, et al., Distinct Proliferative and Differentiated Stages of Murine MC3T3-E1 Cells in Culture: An In Vitro Model of Osteoblast Development, Journal of Bone and Mineral Research, 1992, 7(6):683-692.

Seto, et al., Improved Tendon Radioprotection by Combined Cross-Linking and Free Radical Scavenging, Clinical Orthopaedics and Related Research, 2009, 467(11):2994-3001.

Singh, et al., Gamma Irradiated Bone Allografts Processed from Femoral Heads, Frontiers in Science, 2012, 2(5)119-126.

Smith, et al., MC3T3-EI Osteoblast Attachment and Proliferation on Porous Hydroxyapatite Scaffolds Fabricated with Nanophase Powder, International Journal of Nanomedicine, 2006, 1(2):189-194.

Spicer, et al., Evaluation of Bone Regeneration Using the Rat Critical Size Calvarial Defect, Nature Protocols, 2012, 7(10):1918-1929.

Winkler, et al., One Stage Uncemented Revision of Infected Total Hip Replacement Using Cancellous Allograft Bone Impregnated with Antibiotics, Journal of Bone and Joint Surgery, 2008, 90-B(12):1580-1584.

PCT International Search Report and Written Opinion, PCT/US2017/027861, dated Jul. 5, 2017, 23 pages.

* cited by examiner

SYSTEMS AND METHODS OF RADIOPROTECTION OF ALLOGRAFTS

CROSS-REFERENCE TO RELATED APPLICATIONS

This application is a U.S. National Phase of PCT Application No. PCT/US2017/027861 filed on Apr. 17, 2017, which claims priority from U.S. patent application Ser. No. 62/323,009 filed Apr. 15, 2016.

STATEMENT REGARDING FEDERALLY SPONSORED RESEARCH

Not Applicable.

BACKGROUND OF THE INVENTION

1. Field of the Invention

The current invention relates to systems and methods of protecting allograft against radiation damage. The current invention also relates to systems and methods of incorporating additives such as radioprotectants into allograft tissue.

2. Description of the Related Art

Bone allografts are the preferred method for bone augmentation in about 500,000 orthopaedic surgical procedures in the U.S.. Bone augmentation using natural bone grafts is routinely used in orthopaedic fracture, tumor and joint replacement surgeries to support the repair of defects. Cortical bone grafts are often used as structural bone allografts for orthopaedic applications that require stability, mechanical strength and osteoconductivity.

Autografts are preferred because of their osteoconductivity, serving as a scaffold for new bone growth, and osteoinductivity as they stimulate osteoprogenitor cells to differentiate into osteoblasts. Autografts are also osteogenic by virtue of the presence of live bone cells in the graft material that contribute to bone remodeling. The major disadvantage of autografts is donor site morbidity and infection. In addition, bone stock is limited and cannot be used for cases where large amounts of bone are required.

Allografts are an excellent alternative due to their biocompatibility, strength, and osteoconductivity (Nguyen et al., *Cell and Tissue Banking* 8: 93-105 (2007)). In the U.S., an estimated one million bone grafting procedures are performed annually, about half of which use cadaveric bone allografts. Bone banks use comprehensive donor screening and selection (Delloye et al., *Journal of bone and Joint Surgery* 89: 574-579 (2007)) to minimize the risk of viral and bacterial disease transmission, which is a major concern with allograft use. In some cases, the allograft are irradiated before processing to decrease the risk of disease transmission. Hepatitis C, HIV, and species of *Staphylococcus* are the most common contaminants of bone allografts (Lord et al., *Journal of Bone and Joint Surgery* 70A: 369-374 (1988)). Singh et al. (*Frontiers in Science* 2: 119-126 (2012)) found that 60% of 126 femoral heads obtained from living donors were contaminated with mostly gram-positive bacteria. Fresh allografts are cleaned using solvents and/or solutions of various compounds such as emulsifiers and antibiotics to remove blood, bone marrow, cellular debris while also inactivating bacteria and viruses. Cleaning and decontamination can be done in aseptic environment or terminal sterilization by ethylene oxide, or gamma irradiation are used.

While chemical sterilization such as ethylene oxide sterilization has been shown to minimally impact the mechanical properties of bone allografts, the penetration of various chemicals into bone might not be enough to ensure complete sterility throughout the bone thickness, especially for structural allografts. In addition, infectious agents can be reintroduced during the subsequent handling and packaging of the grafts (Kattaya et al., *Clin Orthop Relat Res* 466: 1796-1803 (2008)). The use of ethylene oxide for sterilizing bone allografts is rare because of the incidence of inflammation of the grafted host tissue. Radiation sterilization is the most effective method of decreasing the bioburden throughout any size bone allograft without leaving chemical residues (Mikhael et al., *J Biomechanics* 41: 2816-2820 (2008)). Low dose radiation (1 kGy) is sufficient to kill 90% of *S. aureus* and *E. coli* and HIV can be inactivated by using a terminal radiation dose of 35 kGy. However, the radiation dose for complete assurance of sterility (SAL=$10^{-6}$) may be higher and the detrimental effects of high doses of radiation (>=25 kGy) on bone allografts are limiting its most effective use for sterilization (Campbell et al., *Aust New Zealand J Surg* 69: 517-521 (1999)). In the dose range of 25-35 kGy used commonly for sterilization, mechanical properties impaired by irradiation include bending and torsion strength, tension fatigue strength, fracture resistance, and compressive strength. In addition, clinical data show that radiation sterilized massive bone allografts fracture at significantly higher rates than unirradiated bone allografts (Lietman, *Clin Orthop Relat Res* 375: 214-217 (2000)).

Therefore, there exists a need for systems and methods for radioprotection of allografts.

SUMMARY OF THE INVENTION

The present invention relates to systems and methods for radioprotection of allografts.

Radiation was shown to result in the degradation of collagen alpha chains, causing increased brittleness. Incorporation of a radioprotectant into bone and soft tissue allografts such as tendons, or meniscus can protect against molecular damage during radiation.

In one embodiment, the invention describes a method of radioprotecting allograft against radiation damage comprising contacting the allograft with radioprotectant, then contacting the radioprotectant-doped allograft with supercritical fluid. In some embodiments, the contact with radioprotectant can be done when the radioprotectant is in pure form, or dissolved in a solvent or solution, or in emulsified form in a solution, gas, fluid or solid. Other compounds can be added to the radioprotectant, solution or emulsion such as antioxidants, antibiotics, growth factors. Some of these other compounds may diffuse into the allograft.

In one embodiment, the invention describes a method of radioprotecting allograft against radiation damage comprising contacting bone allograft with vitamin E, then contacting the vitamin E-doped allograft with supercritical carbon dioxide.

In some embodiments, contacting with radioprotectant to dope the allograft with radioprotectant can be done at a temperature close to or above room temperature. For example, the radioprotectant can be pre-heated/cooled to −10, −5, 0, 5, 10, 15, 20, 25, 30, 35, 40, 45, 50, 55, 60, 65, 70, 75, 80, 85, 90, 95, 100, 105, 110, 115, 120, 125, 130, 135, 140, 145, 1500° C. or above. In some embodiments, the radioprotectant-doped allograft can be contacted with supercritical fluid at close to or above room temperature. For example, it can be contacted with supercritical fluid at 20, 25, 30, 35, 40, 45, 50, 55, 60, 65, 70, 75, 80, 85, 90, 95, 100, 105, 110, 115, 120, 125, 130, 135, 140, 145, 150° C. or above. In some embodiments, the radioprotectant-doped allograft can be contacted with supercritical fluid at close to or above ambient pressure. For example, the pressure can be between 0.00001 to 1000 MPa, or preferably between 0.01 MPa to 100 MPa, most preferably between 1 MPa to 10 MPa.

In some embodiments, the allograft can be used without any further processing other than surface removal of tissue prior to incorporation of radioprotectant. In some embodiments, the allograft can be cleaned by any procedure prior to the incorporation of radioprotectant. In some embodiments, the allograft can be machined, crushed, pulverized, irradiated/sterilized before or after the incorporation of radioprotectant. For example, washing can be done in organic solvents, combination and sequences of organic solvents, aqueous solutions containing optionally emulsifying agents, soaps, oils and similar cleaning agents. For example, an organic solvent comprising chloroform and methanol can be used. In addition, isopropanol can be used for removing extractables.

In some embodiments, during the process of doping with radioprotectant or during the homogenization processes, additional compounds such as bone morphogenic proteins can be introduced into the allograft material to induce or improve osteoconductive and/or osteoinductive properties. Such compounds can also be introduced to regulate the immune reactions to the allograft material. For example, anti-inflammatory compounds such as non-steroid anti-inflammatory drugs and their derivatives can also be introduced into the allograft material. The compounds incorporated may also have more than one effect such as anti-inflammatory and analgesic or anti-inflammatory and antibiotic.

Allografts can be provided in any form to be processed using the methods described herein. Allografts can be provided fresh or fresh-frozen, freeze-dried or demineralized. Allografts can be provided whole or machined or fashioned in any physical form such as cubes, crushed, morselized or in large segments. Allografts can also be provided having undergone previous irradiation or having been cleaned.

These and other features, aspects, and advantages of the present invention will become better understood upon consideration of the following detailed description, drawings, and appended claims.

DETAILED DESCRIPTION OF THE INVENTION

Figure 1:
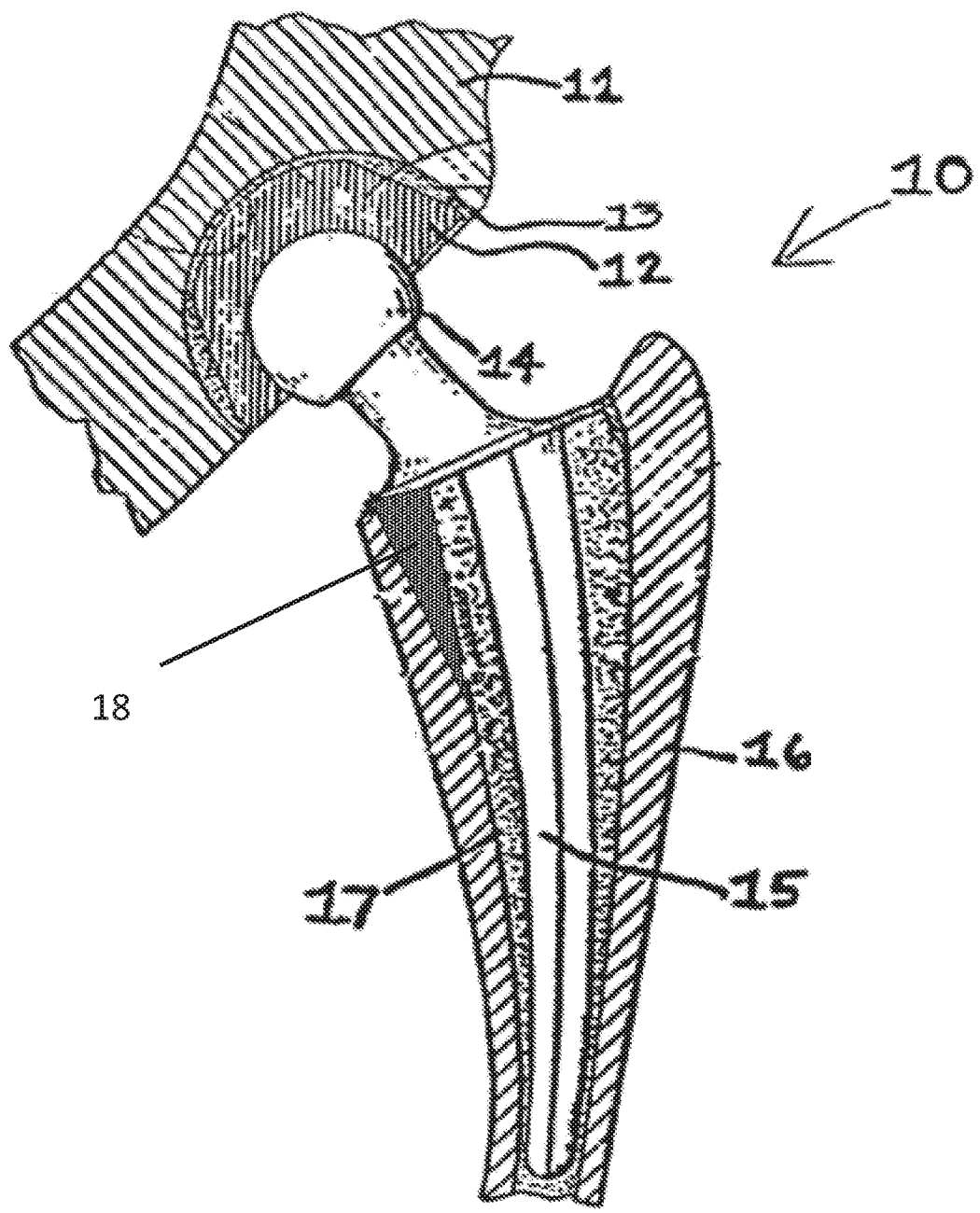
FIG. 1 is a cross-sectional view through the center of a medial hip joint prosthesis with an allograft according to an embodiment of this disclosure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined by the claims. The features illustrated or described in connection with one exemplary embodiment may be combined with the features of other embodiments. Such modifications and variations are intended to be included within the scope of the present invention. The definitions of various terms used to describe the present invention are provided below.

Definitions

The term "additive" is used herein as components added into the allograft. These can be, for example, radioprotectant(s) or therapeutic agent(s). For example, at least one additive is an initiator and a bioactive agent. In another example, the additive is an antibiotic. Additives can be added each into the allograft at a concentration between 0.0001 wt/wt % to 99 wt/wt %, preferably between 0.1 wt/wt % to 20 wt/wt %, more preferably between 0.1 wt/wt % to 5 wt/wt %. An additive can be introduced into the allograft at the same time as the radioprotectant or in a separate process. An additive can be dissolved/emulsified in the radioprotectant or in a solution/emulsion of the radioprotectant. An additive can also be dissolved or carried by supercritical carbon dioxide and can be introduced into the allograft during homogenization in supercritical carbon dioxide.

The term "therapeutic agent" is used herein to refer to what is known in the art, that is, a chemical substance or a mixture thereof capable of eliciting a healing reaction into the human body. A therapeutic agent can be referred to also as a "drug". The therapeutic agent can elicit a response that is beneficial for the human or animal. Examples of therapeutic agents are antibiotics, anti-inflammatory agents, anesthetic agents, anticoagulants, hormone analogs, contraceptives, vasodilators, vasoconstrictors, or other molecules classified as drugs in the art. A therapeutic agent can sometimes have multiple functions. Examples of therapeutic agents are antimicrobials such as Gatifloxacin, gemifloxacin, moxifloxacin, levofloxacin, pefloxacin, ofloxacin, ciprofloxacin, aztreonam, meropenem, imipenem, ertapenem, doripenem, piperacillin, Piperacillin-Tazobactam, Ticarcilin-Clavulanic acid, Ticarcillin, ampicillin-sulbactam, amoxicillin-clavulanic acid, ampicillin-amoxicillin, cloxacillin, nafcillin, oxacillin, methicillin, penicillin V, penicillin G, cefpodox, cefdinir, cefditoren, ceftibuten, cefixime, cefuroxime axetil, cefprozil, cefaclor, loracarbef, cephalexin, cefadroxil, cefepime, ceftazidime, ceftaroline, ceftriaxone, ceftizoxime, cefotaxime, cefuroxime, cefuroxime acetil, cefaclor-CD, cefoxitin, cefotetan, cefazolin, cefdinir, cefditoren pivoxil, cefixime, cefpodoxime proxetil, ceftobiprole, colistimethate, linezolid, quinupristin-dalfopristin, metronidazole, rifampin, fosfomycin, nitrofurantoin, TMP-SMX, trimethoprim, fusidic acid, telavancin, teicoplanin, Vancomycin HCl, vancomycin free base, daptomycin, tigecycline, minocycline, doxycycline, telithromycin, clarithromycin, azithromycin, azithromycin ER, erythromycin, clindamycin, chloramphenicol, amikacin, tobramycin, gentamycin, aztreonam, kanamycin, tetracycline, tetracycline HCl, polymyxin B, rifaximin, tigecycline, amphotericin B, fluconazole, itraconazole, ketoconazole, posaconazole, voriconazole, anidulafungin, caspofungin, flucytosine, micafungin, capreomycin, cycloserine, ethambutol, ethionamide, isoniazid, para-aminosalicylic acid, pyrazinamide, rifabutin, rifapentine, streptomycin, albendazole, artemether/lumefantrine, atovaquone, dapsone, ivermectin, mefloquine, miltefosine, nitazoxanide, proguanil, pytimethamine, praziquantel, tinidazole. Antiviral such as acyclovir, cidofovir, probenecid, entecavir, famciclovir, foscarnet, ganciclovir, oseltamivir, peramivir, ribavirin, rimantadine, telbiudine, valacyclovir, valgancciclovir, abacavir, atazanavir, darunavir, delaviridine, didanosine, efavirenz, emtricitabine, enfuvirtide, etravirine, fosamprenavir, indinavir, lamivudine, lopinavir, maraviroc, nelfinavir, nevirapine, raltegravir, ritonavir, sasquinavir, stavudine, tenofovir, tipranavir, zidovudine. Antifibrinolytics such as ε-aminocaproic acid, tranexamic acid, lysine, aprotinin. Antineoplastics such as mechlrethamine, phenylalanine mustard, chlorambucil, cyclophosphamide, busulfan, triethylene-thiophosphoramide, carmustine, DTIC, methotrexate, 5-fluorouracil, 6-mercaptopurine, vincristine, procarbazone, prednisone, acivicin, aclarubicin, acodazole, acronine, adozelesin, alanosine, alpha-Tgdr, altretamine, ambomycin, amentantrone acetate, aminopterin, aminothiadiazole, amsacrine, anguinide, aniline mustard, anthramycin, azaribine, 5-aza-2'Deoxycytidine, 8-azaguanine.

The term "Antibiotic", is used herein as a type of therapeutic agent, which is used in the treatment and prevention of infectious diseases, specifically bacterial infections. Examples of antibiotics are the antimicrobials listed above.

By "Anti-inflammatory", what is meant is what is known in the art as a type of therapeutic agent used to decrease inflammation. Examples of anti-inflammatories are paracetamol, opioids and salicylates.

By "Analgesic", what is meant is what is known in the art as a type of therapeutic agent used to decrease pain. Examples of analgesics are paracetamol, opioids and salicylates.

"Doping" refers to a process known in the art (see, for example, U.S. Pat. Nos. 6,448,315 and 5,827,904). In this connection, doping generally refers to contacting a material with a component or the solution/emulsion of a component under certain conditions, as set forth herein, for example, doping allograft with an antioxidant under supercritical conditions. "Doping" also refers to introducing additive(s) into the base material in quantities less than 50 v/v %. A material treated in such a way, for example, to incorporate an antioxidant is termed as an "antioxidant-doped" material. The material can be "doped" by other additives as well, such as a crosslinking agent, in which case the material treated in such a way may be termed as "crosslinking agent-doped" material. Alternatively, if the material is doped by one or more radioprotectants, it may be termed "radioprotectant-doped" material.

Doping may also be done by diffusing an additive into a material by immersing the material in additive, by contacting the material with additive in the solid state, by contacting the material with a bath of additive in the liquid state, or by contacting the material with a mixture of the additive in one or more solvents in solution, emulsion, suspension, slurry, aerosol form, or in a gas or in a supercritical fluid. The doping process by diffusion can involve contacting a material, an allograft, a preform, medical implant or device with an additive, such as a radioprotectant, for about an hour up to several days, preferably for about one hour to 24 hours, more preferably for one hour to 16 hours. The doping time can be from a second to several weeks, or it can be 1 minute to 24 hours, or it can be 15 minutes to 24 hours in 15 minute intervals. The medium for the diffusion of the additive (bath, solution, emulsion, paste, slurry and the like) can be cooled down to sub-ambient temperatures, heated to room temperature or up to about 100° C. or more and the doping can be carried out at below room temperature to room temperature or up to about 100° C. or more. Preferably, the antioxidant can be heated to 40° C. and the doping is carried out at 40° C. Or the doping can be carried out at −50° C., −40° C., −30° C., −20° C., −10° C., 0° C., 10° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C.

Although doping is described for one additive above, the same procedure can be used in sequence or simultaneously for multiple additives. For example, Trolox, a more hydrophilic structural relative of alpha-tocopherol (vitamin E) can be dissolved in the vitamin E and doping of allograft material can be done by bringing the material in contact with this mixture. Alternatively, both the Trolox and vitamin E can be emulsified in water and the doping of allograft material can be done by bringing the material in contact with this mixture.

The doped material can be annealed (maintained at a constant temperature other than room temperature) subsequent to doping. The annealing is preferably for about an hour up to several days, more preferably for about one hour to 24 hours, most preferably for one hour to 16 hours. The doping time can be from a second to several weeks, or it can be 1 minute to 24 hours, or it can be 15 minutes to 24 hours in 15 minute intervals. The doped material can be heated to room temperature or up to about 150° C. and the annealing can be carried out at room temperature or up to about 150° C. Preferably, the doped material can be heated to 80° C. and the annealing is carried out at 80° C. Or annealing can be carried out at −50° C., −40° C., −30° C., −20° C., −10° C., 0° C., 10° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C. In the case of a "radioprotectant-doped" material, annealing can cause cross-linking. Annealing can be performed in liquid(s), in air, in other gases such as oxygen, in inert gas, in supercritical fluid(s), in a sensitizing environment or in vacuum. Annealing can also be performed in ambient pressure, above ambient pressure, or below ambient pressure. Annealing can also be performed while the material is immersed in liquid antioxidant, such as vitamin E, or a solution/emulsion of antioxidant(s).

"Radioprotectant" refers to what is known in the art as a compound, which can protect materials against radiation damage. Radiation energy can be imparted to materials in different forms, for example ultraviolet radiation, thermal radiation, ionizing radiation, particle radiation, visible light radiation, infrared radiation and the like. Radiation damage can be in different constituents of a material, for example cellular or non-cellular components of a tissue can be affected by the radiation and the radiation energy to which they have been exposed. Radioprotectants are molecules that can limit this damage to any degree. For example, the collagen network of a natural tissue such as bone can be disrupted by radiation; a radioprotectant such as vitamin E (a single tocopherol or a mixture of different tocopherols) can reduce or eliminate this disruption.

"Allograft" refers to what is known in the art, that is, a tissue graft from one person to another. Allograft can refer to different tissues, for example bone, cartilage, muscle, nerve, or vascular tissues.

The term "packaging" refers to the container or containers in which a medical implant is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

The term "sterile" refers to a condition of an object, for example, an interface or a material or a medical implant containing interface(s), wherein the interface(s) are sufficiently sterile to be medically acceptable, i.e., will not cause an infection or require revision surgery. The object, for example a medical implant, can be sterilized using ionizing radiation or gas sterilization techniques. Gamma sterilization is well known in the art. Electron beam sterilization is also used. Ethylene oxide gas sterilization and gas plasma sterilization are also used. Autoclaving is another method of sterilizing medical implants. Exposure to solvents or supercritical fluids for sufficient to kill infection-causing microorganisms and/or their spores can be a method of sterilizing. "Sterilization" refers to methods to which the medical implants are exposed such that sterility is achieved.

The term 'irradiation' refers to what is known in the art as exposing a material to radiation, for example ionizing radiation such as a gamma, electron, X-ray or ultraviolet (UV) radiation. 'Radiation sterilization' refers to a radiation process intended to achieve sterility in a material as a result of irradiation, for example exposing allograft to gamma irradiation to sterilize the material. The radiation dose used can be from 0.0001 kGy to 100000 kGy, or 0.1 kGy to 1000 kGy, or from 1 kGy to 300 kGy, or about 15 kGy, or about 25 kGy, or about 50 kGy. The radiation dose rate can be from 0.001 kGy/min to 100000 kGy/min, or from 0.1 kGy/min to 100 kGy/min, or from 1 kGy/min to 50 kGy/min, or about 25 kGy/min, or about 10 kGy/min, or about 100 kGy/min. Irradiation can be done in air, in vacuum, or partial gas environments, for example mixtures of oxygen and nitrogen. It can also be done in inert gas or partial inert gas. It can also be done at ambient temperature, or below or above ambient temperature. It can be done at elevated temperatures above ambient temperature. Irradiation temperature can be from −100° C. to 1000° C., or from 0° C. to 500° C., or from 20° C. to 200° C., or from 25° C. to 150° C., or at about 25° C., or about 40° C., or about 70° C.

"Collagen cross-linking agent" refers to a compound which can result in increased covalent bonding of collagen chains. The term 'cross-linking' refers to in general what is known in the art as processes that result in the covalent bonding of the parts of a material, for example polymer chains in a polymeric material. Examples of cross-linking agents for natural proteins include but are not limited to formaldehyde, glutaraldehyde, genipin, rose bengal.

"Supercritical fluid" refers to what is known in the art as a state for a compound above the critical temperature and pressure of that compound. In this supercritical state, the fluid exhibits diffusive properties like a gas and dissolution properties like a liquid. For example, carbon dioxide is a supercritical fluid above about 31° C. and 7.4 MPa and water is a supercritical fluid above about 374° C. and 22 MPa. Contact with supercritical fluid can be used to extract specific components out of material in contact with it or it can be used to diffuse specific components into the material in contact with it. During contact of material with supercritical fluids, other additives can be injected into the chamber and dissolved or dispersed in the supercritical fluid. As such, contact with these additives is also possible during supercritical fluid contact. Additives such as bone morphogenic proteins, antioxidants, cross-linking agents, free radical scavengers, fillers, anti-inflammatories, antibiotics can be added in pure form, in solution, or in dispersion.

The term "homogenization" refers to a processes whose purpose is to make the concentration profile of the radioprotectant or other additives throughout the interior of a radioprotectant and/or additive-doped material more spatially uniform. The doping can be followed by an additional step of "homogenization", which refers to a step in air or in anoxic environment to improve the spatial uniformity of the concentration within the material, medical implant or device. Homogenization also can be carried out before and/or after the irradiation step. The homogenization step can include heating. Radioprotectant-doped material can be homogenized at a temperature below or above room temperature for a desired period of time, for example, the radioprotectant-doped material can be homogenized for about an hour to several days at room temperature to about 400° C. Preferably, the homogenization is carried out at 10° C. to 100° C., more preferably 20° C. to 60° C., most preferably 40° C. Homogenization is preferably carried out for about one hour to several days to two weeks or more, more preferably about 2 hours to 36 hours or more, more preferably about 24 hours, or more preferably about 12 hours. More preferably, the homogenization is carried out at about 40° C. for about 24 hours or at about 40° C. for about 12 hours. The material, medical implant or device may be kept in an inert atmosphere (nitrogen, argon, and/or the like), under vacuum, or in air during the homogenization process. The homogenization also can be performed in a chamber with supercritical fluids such as carbon dioxide or the like. The pressure of the supercritical fluid can be about 10 to about 3000 psi or more, more preferably about 850-1500 psi.

The term "antioxidant" refers to what is known in the art as additives that protect the host material against oxidation for example under various aggressive environments, such as during high temperature, radiation or high oxygen concentration exposure etc. Antioxidants, which may also scavenge free radical can be chosen from but not limited to glutathione, lipoic acid, vitamins such as ascorbic acid (vitamin C), vitamin B, vitamin D, vitamin-E, tocopherols (synthetic or natural, alpha-, gamma-, delta-), acetate vitamin esters, water soluble tocopherol derivatives, tocotrienols, water soluble tocotrienol derivatives; melatonin, carotenoids including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox™ family; Irganox® and Irganox® B families including Irganox® 1010, Irganox® 1076, Irganox® 1330, Irganox® 1035; Irgafos® family; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. They can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination. Also, antioxidants can be used with in conjunction with other additives such as hydroperoxide decomposers.

Irganox®, as described herein refers to a family of antioxidants manufactured by Ciba Specialty Chemicals. Different antioxidants are given numbers following the Irganox® name, such as Irganox® 1010, Irganox® 1035, Irganox® 1076, Irganox® 1098, etc. Irgafos® refers to a family of processing stabilizers manufactured by Ciba Specialty Chemicals. Irganox® family has been expanded to include blends of different antioxidants with each other and with stabilizers from different families such as the Irgafos family. These have been given different initials after the Irganox® name, for instance, the Irganox® HP family are synergistic combinations of phenolic antioxidants, secondary phosphate stabilizers and the lactone Irganox® HP-136. Similarly, there are Irganox® B (blends), Irganox® L (aminic), Irganox® E (with vitamin E), Irganox® ML, Irganox® MD families. Herein we discuss these antioxidants and stabilizers by their tradenames, but other chemicals with equivalent chemical structure and activity can be used. Addition, these chemicals can be used individually or in mixtures of ant composition. Some of the chemical structures and chemical names of the antioxidants in the Irganox® family are listed in Table 1.

TABLE 1

Chemical names and structures of some antioxidants trademarked under the Irganox ® name.

| Tradename | Chemical Name | Chemical Structure |
| --- | --- | --- |
| Irganox ® 1010 | Tetrakis[methylene(3,5-di-tert-butylhydroxyhydrocinnamate)] methane | $\left[ C-CH_2-O-\overset{O}{\underset{\|}{C}}-CH_2-CH_2-\text{(3,5-di-tert-butyl-4-hydroxyphenyl)} \right]_4$ <br> 1178 g/mol |
| Irganox ® 1035 | Thiodiethylene bis[3-[3,5-di-tert-butyl-4-hydroxyphenyl]propionate] | (structure shown) |
| Irganox ® 1076 | Octadecyl 3,5-di-tert-butyl-4-hydroxylhydrocinnamate | (structure shown with $C_{18}H_{37}$) |
| Irganox ® 1098 | N,N'-hexane-1,6-diylbis(3-(3,5-di-tert-butyl-4-hydroxyphenylpropionamide)) | |
| Irganox ® 1135 | Benzenepropanoic acid, 3,5-bis(1,1-dimethyl-ethyl)-4-hydroxy-•$C_7$-$C_9$ branched alkyl esters | (structure shown with i-$C_8H_{17}$) <br> 390 g/mol |

TABLE 1-continued

Chemical names and structures of some antioxidants trademarked under the Irganox ® name.

| Tradename | Chemical Name | Chemical Structure |
|---|---|---|
| Irganox ® 1330 | 1,3,5-tris(3,5-di-tert-butyl-4-hydroxybenzyl)-2,4,6-trimethylbenzene | 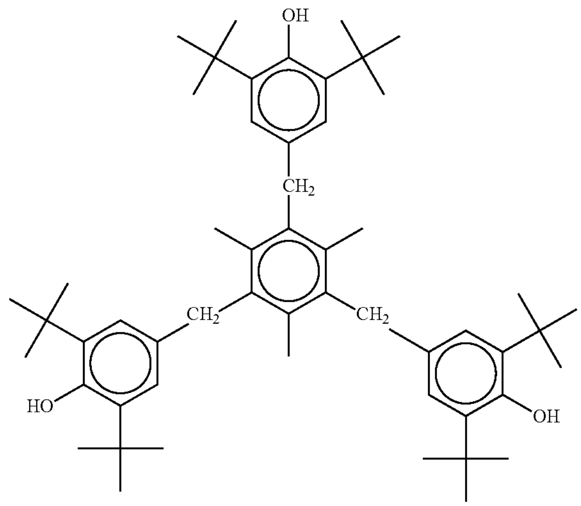 |
| Irganox ® 1520 | | 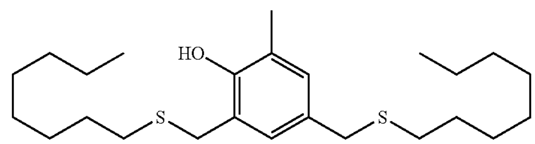 [SMILES: CCCCCCCCSCc1cc(C)c(O)c(CSCCCCCCCC)c1] |
| Irganox ® 1726 | 2,4-bis(dodecylthiomethyl)-6-methylphenol | 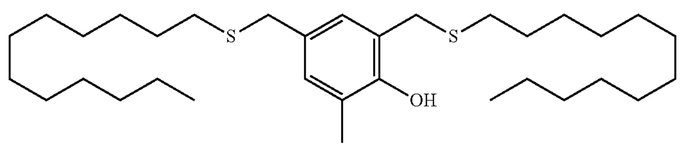 [SMILES: CCCCCCCCCCCCSCc1cc(C)c(O)c(CSCCCCCCCCCCCC)c1] |
| Irganox ® 245 | Triethylene glycol bis(3-tert-butyl-4-hydroxy-5-methylphenyl)propionate | 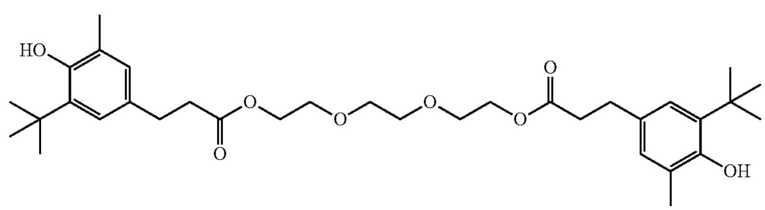 [SMILES: Cc1cc(CCC(=O)OCCOCCOCCOC(=O)CCc2cc(C)c(O)c(C(C)(C)C)c2)cc(C(C)(C)C)c1O] |
| Irganox ® 3052 | 2,2'-methylenebis(4-methyl-6-tert-butylphenol)monoacrylate | 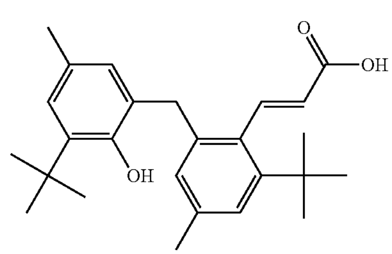 [SMILES: Cc1cc(Cc2cc(C)cc(C(C)(C)C)c2/C=C/C(=O)O)c(O)c(C(C)(C)C)c1] |

TABLE 1-continued

Chemical names and structures of some antioxidants trademarked under the Irganox® name.

| Tradename | Chemical Name | Chemical Structure |
|---|---|---|
| Irganox® 3114 | 1,3,5-Tris(3,5-di-tert-butyl-4-hydroxybenzyl)-1,3,5-triazine-2,4,6(1H,3H,5H)-trione | 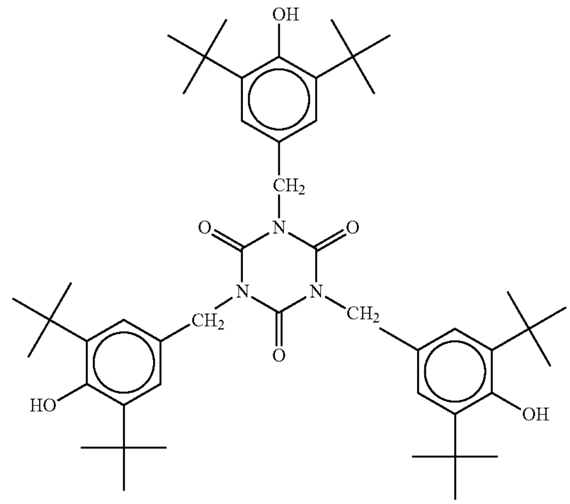 |
| Irganox® 5057 | Benzenamine,N-phenyl-,reaction products with 2,4,4-trimethylpentene | R, $R_1$ = H, $C_4H_9$, or $C_8H_{17}$ and other alkyl chains |
| Irganox® 565 | 2,4-bis(octylthio)-6-(4-hydroxy-3,5-di-tert-butylanilino)-1,3,5-triazine | 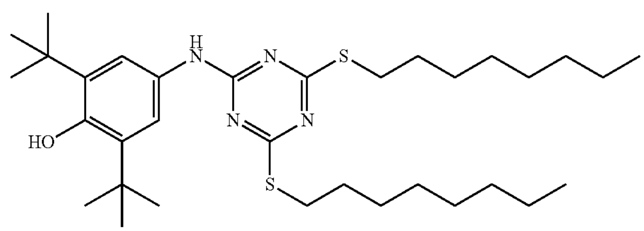 [SMILES: CCCCCCCCSc1nc(Nc2cc(C(C)(C)C)c(O)c(C(C)(C)C)c2)nc(SCCCCCCCC)n1] |
| Irganox® HP-136 | 5,7-di-t-butyl-3-(3,4 di-methylphenyl)-3H-benzofuran-2-one | 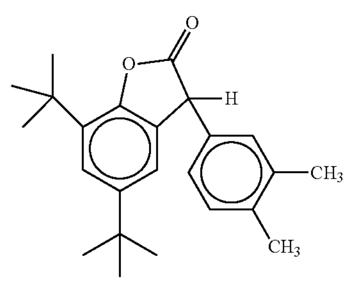 |
| Irgafos® 168 | Tris(2,4-di-tert-butylphenyl)phospite | 646.9 g/mol |

"Cleaning" refers to processes whose aims are to remove certain components from material exposed to these processes. Cleaning can be done by contacting material with aqueous media including solutions and emulsions, organic and inorganic solvents, other media such as solid emulsions, slurries, aerosols or supercritical fluids. Common cleaning processes for bone allograft, for example, can aim to remove cellular material or non-cellular material to remove components that can elicit an immune reaction from the host when in contact with allograft or to remove structural components to change the morphology of the allograft, for example to make it more porous. Cleaning processes can include contacting material with organic solvents or mixtures such as methanol and chloroform, or isopropyl alcohol. They can also include contacting material with aqueous solutions or emulsions with cleaning agents such as emulsifiers, nonionic surfactants, soaps, fatty acids, and other acids and alkali components. They can also include components such as chelators, or mineral acids designed to bind specific components such as metal ions. During the cleaning processes, molecules other than the cleaning agents in the cleaning medium can diffuse to varying degrees into the material.

The term 'emulsifying agent' refers to compounds which are amphiphilic; that is, have affinity to both hydrophilic and hydrophobic solvents. They can enable hydrophobic molecules which have little or no solubility in water to be dissolved or dispersed uniformly and stably in aqueous solutions. Examples of emulsifying agents include monoglycerides, diglycerides, esters or polyethylene glycol, polyethylene glycols, sorbitan esters, polysorbates. Some commercial examples of polysorbates are Tween 20, which is a polyoxyethylene derivative of sorbitan monolaurate and Tween 80, which is a polyoxyethylene derivative of sorbitan monooleate.

The term 'medical implant' refers to materials or devices made for the purpose of implantation in a living body, for example and animal or human body. The medical implants include but are not limited to bone, tendon, ligament, meniscus, cartilage allografts. The term "permanent device" refers to what is known in the art that is intended for implantation in the body for a period longer than several months.

What is meant by room temperature is between 15° C. and 30° C.

The terms "about" or "approximately" in the context of numerical values and ranges refers to values or ranges that approximate or are close to the recited values or ranges such that the invention can perform as intended, such as utilizing a method parameter (e.g., time, dose, dose rate/level, and temperature), having a desired concentration of additive, as is apparent to the skilled person from the teachings contained herein. This is due, at least in part, to the varying properties of compositions. Thus, these terms encompass values beyond those resulting from systematic error. These terms make explicit what is implicit, as known to the person skilled in the art.

The term 'heating' refers to bringing a material to a temperature, generally a temperature above that of its current state. It can also refer to maintaining said temperature for a period of time, that is, in some instances it can be used interchangeably with 'annealing'. Heating can be done at any rate. The heating rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals. The heating can be done for any duration. Heating time can be from 0.1 minutes to 100 years, or from 1 minute to 24 hours, or from 1 minute to 12 hours, or 30 minutes to 10 hours, or 5 hours, or 6 hours, or 8 hours.

The term 'cooling' refers to bringing a material to a temperature, generally a temperature below that of its current state. It can also refer to maintaining said temperature for a period of time, that is, in some instances it can be used interchangeably with 'annealing'. Cooling can be done at any rate. The cooling rate can be from 0.001° C./min to 1000° C./min, or it can be between 0.1° C./min to 100° C./min, or it can be from 0.5° C./min to 10° C./min, or it can be any rate from 1° C./min to 50° C./min in 1° C. intervals, or 2.5° C./min. The cooling can be done for any duration. Cooling time can be from 0.1 minutes to 100 years, or from 1 minute to 24 hours, or from 1 minute to 12 hours, or 30 minutes to 10 hours, or 1 hours, or 2 hours, or 5 hours, or 6 hours, or 8 hours.

The term 'osteoconduction' refers to an ability of material to enable the osteoblasts close to or in contact with it when the graft material is inserted into a bony defect to use the material as a scaffold to generate new bone. The term 'osteoinduction' refers to the stimulation of osteoprogenitor cells to differentiate into osteoblasts that then begin new bone formation. Fresh-frozen allografts with biological/cellular components or allografts incorporated with necessary components such as bone morphogenic proteins or BMPs can be osteoinductive.

Methods of Radioprotection of Allograft

In one aspect, the invention describes methods of making sterilized allograft comprising (a) providing an allograft, (b) contacting the allograft with radioprotectant for a period of time, thereby forming a radioprotectant-doped allograft; (c) contacting the radioprotectant-doped allograft with supercritical fluid for a period of time; thereby forming a radioprotectant doped and homogenized allograft; and (d) irradiating radioprotectant-doped and homogenized allograft; thereby forming sterilized allograft.

In one aspect, the invention describes methods of making sterilized allograft comprising (a) providing an allograft, (b) contacting the allograft with at least one radioprotectant for a period of time, thereby forming a radioprotectant-doped allograft; (c) contacting the radioprotectant-doped allograft with supercritical fluid for a period of time; thereby forming a radioprotectant doped and homogenized allograft; and (d) irradiating radioprotectant-doped and homogenized allograft; thereby forming sterilized allograft.

In one aspect, the invention describes methods of making a medical implant comprising (a) providing an allograft, (b) contacting the allograft with at least one radioprotectant for a period of time, thereby forming a radioprotectant-doped allograft; (c) contacting the radioprotectant-doped allograft with supercritical fluid for a period of time; thereby forming a radioprotectant doped and homogenized allograft; and (d) irradiating the radioprotectant-doped and homogenized allograft.

In one aspect, the invention describes methods of making sterilized allograft comprising (a) providing an allograft, (b) contacting the allograft with at least one radioprotectant and at least one more additive for a period of time, thereby forming a radioprotectant-doped allograft; (c) contacting the radioprotectant-doped allograft with supercritical fluid for a period of time; thereby forming a radioprotectant doped and homogenized allograft; and (d) irradiating radioprotectant-doped and homogenized allograft; thereby forming sterilized allograft.

In one aspect, the invention describes methods of making a medical implant comprising (a) providing an allograft, (b) contacting the allograft with at least one radioprotectant and at least one more additive for a period of time, thereby forming a radioprotectant-doped allograft; (c) contacting the radioprotectant-doped allograft with supercritical fluid for a period of time; thereby forming a radioprotectant doped and homogenized allograft; and (d) irradiating radioprotectant-doped and homogenized allograft; thereby forming sterilized allograft.

In one aspect, the invention describes methods of making a medical implant comprising (a) providing an allograft, (b)

contacting the allograft with at least one radioprotectant and at least one antibiotic for a period of time, thereby forming a radioprotectant-doped allograft; (c) contacting the radioprotectant-doped allograft with supercritical fluid for a period of time; thereby forming a radioprotectant doped and homogenized allograft; and (d) irradiating radioprotectant-doped and homogenized allograft; thereby forming sterilized allograft. The contacting with the additives can be done at the same time or consecutively or in a partially overlapping fashion.

In any of the embodiments, the described steps can be performed once or any or all of the steps can be repeated.

In one aspect, the invention describes methods of making sterilized bone allograft comprising (a) providing an allograft, (b) contacting the allograft with vitamin E for a period of time, thereby forming a vitamin E-doped allograft; (c) contacting the vitamin E-doped allograft with supercritical fluid for a period of time; thereby forming a vitamin E-doped and homogenized allograft; and (d) irradiating the vitamin E-doped and homogenized allograft; thereby forming sterilized allograft.

In one aspect, the invention describes methods of making sterilized bone allograft comprising (a) providing an allograft, (b) contacting the allograft with a mixture of Trolox (6-hydroxy-2,5,7,8-tetramethylchroman-2-carboxylic acid) and vitamin E for a period of time, thereby forming a radioprotectant-doped allograft; (c) contacting the radioprotectant-doped allograft with supercritical fluid for a period of time; thereby forming a radioprotectant-doped and homogenized allograft; and (d) irradiating the radioprotectant-doped and homogenized allograft; thereby forming sterilized allograft.

By using the methods described by the invention, a terminally radiation sterilized allograft can be protected against radiation damage. A terminal radiation dose of 1, 5, 10, 15, 20, 25, 30, 35, 40, 45 or 50 kGy or more can be used. Radiation damage can be determined as decreased mechanical properties, damage to the collagen structure, or damage to its osteoconductive or osteoinductive properties.

In some embodiments, the invention describes methods of making sterilized bone allograft comprising (a) providing an allograft, (b) contacting the allograft with collagen cross-linking agent(s); (c) contacting the allograft with a mixture of radioprotectant(s) for a period of time, thereby forming a radioprotectant-doped allograft; (d) contacting the radioprotectant-doped allograft with supercritical fluid for a period of time; thereby forming a radioprotectant-doped and homogenized allograft; and (e) irradiating the radioprotectant-doped and homogenized allograft, thereby forming sterilized allograft.

In one aspect, the invention describes methods of making sterilized allograft comprising (a) providing an allograft, (b) cleaning the allograft; (c) contacting the allograft with radioprotectant for a period of time, thereby forming a radioprotectant-doped allograft; (d) contacting the radioprotectant-doped allograft with supercritical fluid for a period of time; thereby forming a radioprotectant doped and homogenized allograft; and (e) irradiating radioprotectant-doped and homogenized allograft, thereby forming sterilized allograft.

In one aspect, the invention describes methods of making sterilized allograft comprising (a) providing an allograft, (b) cleaning the allograft; (c) contacting the allograft with radioprotectant and optionally other additive(s) for a period of time, thereby forming a radioprotectant-doped allograft; (d) contacting the radioprotectant-doped allograft with supercritical fluid for a period of time; thereby forming a radioprotectant doped and homogenized allograft; and (e) irradiating radioprotectant-doped and homogenized allograft, thereby forming sterilized allograft.

In one aspect, the invention describes methods of making sterilized allograft comprising (a) providing an allograft, (b) cleaning the allograft; (c) contacting the allograft with radioprotectant for a period of time, thereby forming a radioprotectant-doped allograft; (d) contacting the radioprotectant-doped allograft with supercritical fluid for a period of time optionally in the presence of other additive(s); thereby forming a radioprotectant doped and homogenized allograft; and (e) irradiating radioprotectant-doped and homogenized allograft, thereby forming sterilized allograft.

In any of the aspects, the bone allograft can be crushed, machined or whole.

In any of the aspects, the allograft can be a cartilaginous allograft selected from the group consisting of a tendon, a ligament, an articular cartilage, an auricular cartilage, and a meniscus allograft. The cartilaginous graft can be processed, machined or whole.

In any of the aspects, the provided allograft can be irradiated.

In any of the aspects, the radioprotectant can be a mixture containing vitamin E. The radioprotectant can also be selected from the group consisting of pure, in solution, and in an emulsion.

In any of the aspects, the allograft can be contacted with radioprotectant at about room temperature. The allograft can also be contacted with the radioprotectant at a temperature between room temperature and 60° C.

In any of the aspects, the supercritical fluid can be carbon dioxide. The radioprotectant-doped allograft can be contacted with a supercritical fluid at a temperature between room temperature and 100° C. The radioprotectant-doped allograft can be contacted with the supercritical fluid for a time between 4 and 24 hours.

In any of the aspects, a terminal irradiation dose can be below 30 kGy. A terminal irradiation dose can also be between 30 and 50 kGy. A terminal irradiation dose can also be above 50 kGy.

In any of the aspects, the allograft can be a cartilaginous allograft from the group consisting of a tendon, ligament, articular cartilage, auricular cartilage, and meniscus allograft. The cartilaginous graft can be processed, machined or whole.

In any of the aspects, the at least one additive can an antibiotic. The antibiotic can be vancomycin. The antibiotic can also be gentamicin.

In any of the aspects, the at least one additive can be an anti-inflammatory agent. The at least one additive can be an analgesic.

In one aspect, the invention describes a method of protecting collagen cross-links in a radiation sterilized allograft, the method comprising (a) providing an allograft; (b) cleaning the allograft; (c) contacting the allograft with at least one radioprotectant thereby creating a radioprotectant-doped allograft; (d) contacting the radioprotectant-doped allograft with a supercritical fluid thereby obtaining a radioprotectant doped and homogenized allograft; and (e) irradiating the radioprotectant doped and homogenized allograft.

In one aspect, the invention describes a method of making a medical implant with preserved collagen cross-linking, the method comprising, (a) providing an allograft; (b) cleaning the allograft; (c) contacting the allograft with radioprotectant(s); (d) contacting the radioprotectant-doped allograft with a supercritical fluid thereby obtaining a radioprotectant doped and homogenized allograft; and (e) irradiating the radioprotectant doped and homogenized allograft In one aspect, the allograft can be comprised of different tissues. The allograft can be comprised of bone and tendon.

In one aspect, the invention describes a method of making an allograft with improved integration to host tissue, the method comprising: (a) providing an allograft; (b) cleaning the allograft; (c) contacting the allograft with at least one radioprotectant, thereby obtaining a radioprotectant-doped allograft; and (d) contacting the radioprotectant-doped allograft with a supercritical fluid thereby obtaining a radioprotectant doped and homogenized allograft; and (e) irradiating the radioprotectant doped and homogenized allograft.

In one aspect, the invention describes an allograft with improved integration to host tissue made by a method comprising: (a) providing an allograft; (b) cleaning the allograft; (c) contacting the allograft with at least one radioprotectant and optionally other additive(s), thereby obtaining a radioprotectant-doped allograft; and (d) contacting the radioprotectant-doped allograft with a supercritical fluid optionally in the presence of other additive(s); thereby obtaining a radioprotectant doped and homogenized allograft; and (e) irradiating the radioprotectant doped and homogenized allograft.

In one aspect, the invention describes a method of making an allograft with improved integration to host tissue, the method comprising: (a) providing an allograft; (b) cleaning the allograft; (c) contacting the allograft with at least one radioprotectant and optionally other additive(s), thereby obtaining a radioprotectant-doped allograft; and (d) contacting the radioprotectant-doped allograft with a supercritical fluid optionally in the presence of other additive(s), thereby obtaining a radioprotectant doped and homogenized allograft; and (e) Irradiating the radioprotectant doped and homogenized allograft.

In one aspect, the invention describes a method of making an allograft with improved integration to host tissue, the method comprising: (a) providing an allograft; (b) cleaning the allograft; (c) contacting the allograft with at least one radioprotectant and at least one antibiotic, thereby obtaining a radioprotectant and antibiotic-doped allograft; and (d) contacting the radioprotectant-doped allograft with a supercritical fluid, thereby obtaining a radioprotectant and antibiotic-doped and homogenized allograft; and (e) irradiating the radioprotectant and antibiotic-doped and homogenized allograft.

In any of the aspects, the doping can be done at room temperature. The doping can also be done between room temperature and 60° C. The homogenization is done at about 40° C. The doping can be done under inert atmosphere. The homogenization in supercritical carbon dioxide can be done at about 85 bar. The doping can be done for about 6 hours. The doping can be done for less than 6 hours. The homogenization in supercritical fluid can be done for about 24 hours. The homogenization in supercritical carbon dioxide can be done for less than 24 hours.

In some embodiments, the described processes can be performed sequentially or some processes can be performed simultaneously. Also, the steps comprising a method can be repeated. Or allografts which have been processed by different methods described herein can be combined prior to or after irradiation.

Systems of Radioprotection of Allograft

In some embodiments, a material for the repair of a bone defect is provided. The material can comprise a radioprotectant-doped allograft. The radioprotectant-doped allograft can be created by contacting an allograft with at least one radioprotectant. The radioprotectant-doped allograft can also be contacted with a supercritical fluid. The radioprotectant-doped allograft that has been contacted by the supercritical fluid can also be irradiated.

In some embodiments of the material for the repair of a bone defect, the allograft can be a bone allograft. In some embodiments, the bone allograft can be cancellous or cortical, in other embodiments, the bone allograft can be crushed, machined or whole.

In some embodiments of the material for the repair of a bone defect, the allograft can be a cartilaginous allograft selected from the group consisting of a tendon, ligament, articular cartilage, auricular cartilage, and meniscus allograft. In other embodiments, the cartilaginous allograft can be processed, machined or whole. In other embodiments, an allograft can be comprised of different tissues, for example bone and tendon or bone and cartilage.

In other embodiments, a prosthetic system for implantation in a subject is provided. The prosthetic system can comprise at least one radioprotectant-doped allograft. In other embodiments, the prosthetic system can comprise a prosthetic implant, and a radioprotectant-doped allograft. The radioprotectant-doped allograft can be created by contacting an allograft with at least one radioprotectant and optionally with other additive(s). In some embodiments, the radioprotectant-doped allograft can also be contacted with a supercritical fluid optionally in the presence of other additive(s). The radioprotectant-doped allograft contacted by the supercritical fluid can also be irradiated.

In some embodiments, the prosthetic system can be configured to replace a defect in a joint of a subject. Non-limiting examples of joints include an ankle, a knee, a hip, a wrist, an elbow, a shoulder, a finger, and a toe. In other embodiments, the prosthetic system is configured to replace a defect in a spine.

In an exemplary embodiment, a prosthetic system in the form of a medical prosthesis, specifically a hip joint prosthesis is generally illustrated at 10 in FIG. 1. The prosthesis shown has a conventional ball head 14 connected by a neck portion to a stem 15 which is mounted by conventional bone cement 17 to the femur 16. The radius of the ball head closely conforms to the inner cup radius of an acetabular cup 12 which can be mounted in cement 13 directly to the pelvis 11. Alternatively, a metallic acetabular shell can be cemented to the pelvis 11 and the acetabular cup 12 can form a coating or liner connected to the metallic acetabular shell by means as are known in the art. A material 18 for the repair of a bone defect is shown to be implanted between the femur 16 and the bone cement 17 to provide support to the prosthesis 10. The material 18 for the repair of a bone defect can be a radioprotectant-doped allograft which can be created according to any of the methods or examples detailed in this disclosure.

The specific form of the prosthesis can vary greatly as known in the art. Many hip joint constructions are known and other prostheses such as knee joints, shoulder joints, ankle joints, elbow joints and finger joints are known. In all cases, a radioprotectant-doped allograft can be implanted to provide support to the prosthesis and minimize radiation damage caused during sterilization. The radioprotectant-doped allograft can be created according to any of the methods or examples detailed in this disclosure.

Figure 2:
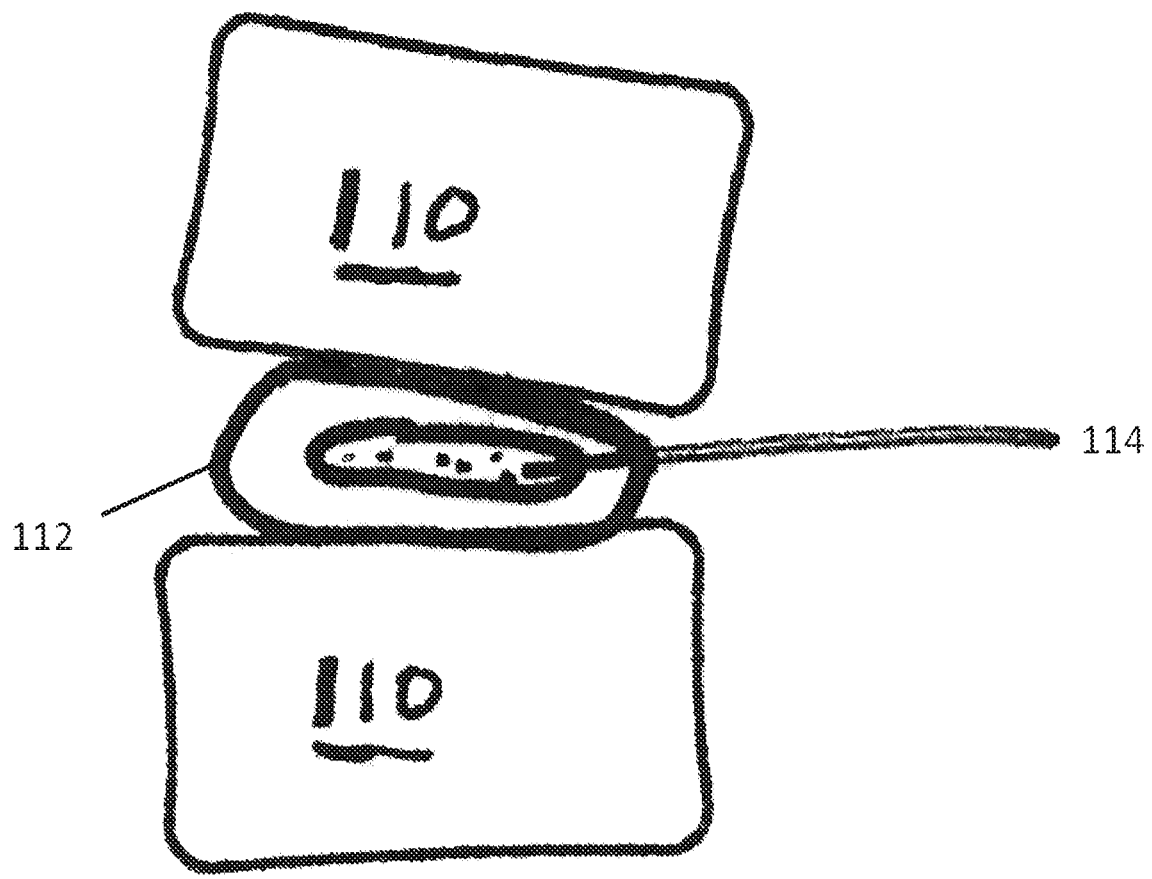
FIG. 2 is a cross sectional view of a spinal cage with an allograft according to an embodiment of this disclosure.

In another exemplary embodiment, FIG. 2 shows a spinal cage 112 positioned between two vertebrae 110 which incorporates a material 114 for the repair of a bone defect. In some embodiments, the material 114 for the repair of a bone defect can be a radioprotectant-doped allograft. The radioprotectant-doped allograft can be implanted to minimize radiation damage caused during sterilization. The radioprotectant-doped allograft can be created according to any of the methods or examples detailed in this disclosure.

In some embodiments, the biological activity of parts of the allograft can be protected against the destructive effects of radiation for sterilization or other purposes. In this case, the integration between host and allograft can be improved by incorporating radioprotectant(s) and optionally other additive(s) into the allograft. The integration of host and allograft, for example for bone, can be measured by assessing the lucency at the interface(s) of the two tissues using an imaging technique such as micro-computed tomography or µ-CT.

The invention is further illustrated in the following Examples which are presented for purposes of illustration and not of limitation.

EXAMPLES

Example 1

Radioprotection of Bone Allograft Using Vitamin E Doping and Supercritical Carbon Dioxide Homogenization Vitamin E, Tween 80, chloroform, methanol, calcium phosphate, and genipin were all purchased from Sigma-Aldrich, Inc., St Louis, USA. Bovine tibias were obtained from Animal Technologies, Texas, USA. Terminal sterilization using a 3 MeV electron beam was conducted using a Van de Graaf generator at the MIT High Voltage Research Laboratory, Cambridge, Mass., USA.

Figure 3:
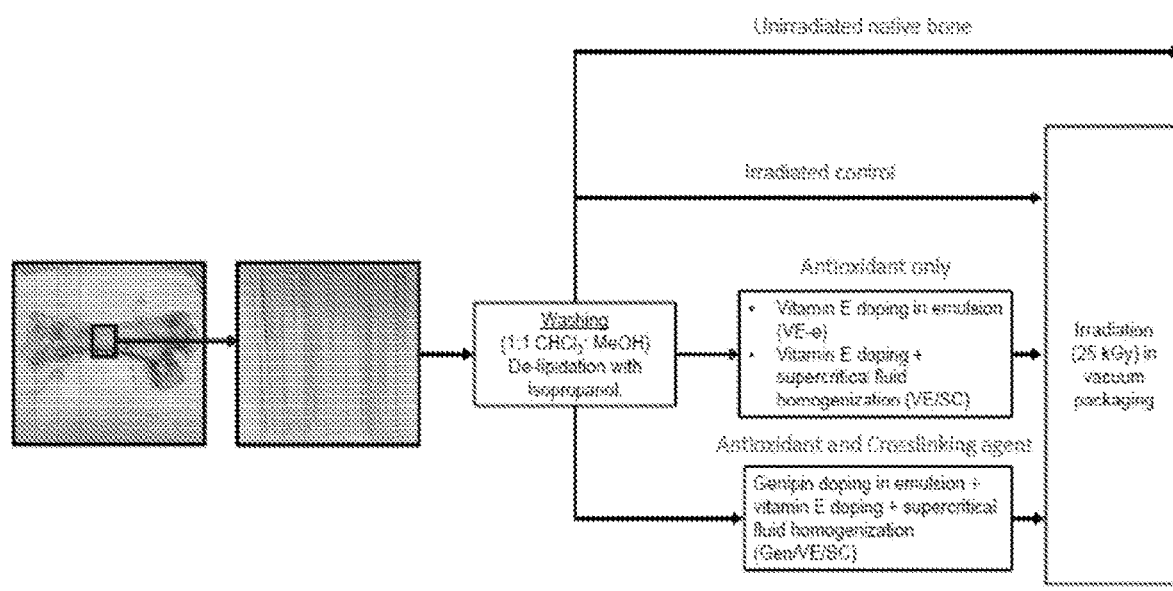
FIG. 3 is a schematic summarizing the processing of the bone allografts used in a study of this disclosure.

Bone Graft Machining and Cleaning:

The diaphysis of bovine tibia was machined into 3.7 mm×3.7 mm×55 mm blocks for bending testing (FIG. 3) and to 4 mm×10 mm×50 mm for IZOD impact testing. All samples were then washed with isopropanol for 2 hours and then delipidized in 1:1 chloroform:methanol for 48 hours. Samples were then divided into subgroups for subsequent treatment with the radioprotectant (vitamin E) and the radioprotectant+crosslinking agent (genipin) (FIG. 3).

Preparation of Emulsified Vitamin E:

In an Erlenmeyer flask, 1.875 gram vitamin E and 7.5 gram Tween 80 were mixed, heated at 70° C. and stirred for 30 minutes. The resulting mixture was added to 110 gram of deionized water (DI) at 70° C. 7.5 gram ethanol was then added to the mixture and heated under reflux for 2 hours until a homogenous emulsion was obtained.

Treatment of Allograft with the Vitamin E Emulsion:

One group of delipidized bovine tibia was fully immersed in the vitamin E emulsion supplemented with 300 mg/L calcium phosphate for 2 weeks at 25° C. under constant stirring. The emulsion was replaced every 2 days. At the completion of the impregnation, samples were removed from the emulsion, washed with saline, and packaged in vacuum bags and irradiated to 25 kGy.

Treatment of Allograft with Antioxidant Doping Followed by Supercritical Fluid Homogenization:

Another group of delipidized bovine tibia was fully immersed in the vitamin E at 55° C. for 6 hours. Samples were then transferred to a supercritical fluid chamber. The samples that were previously doped with vitamin E were then treated in supercritical $CO_2$ at 40° C. and 85 bar for 24 hours. Samples were packaged in vacuum bags and irradiated to 25 kGy.

Treatment of Allograft with Cross-Linking Agent and with Radioprotectant:

Another group of delipidized bovine tibia was fully immersed in a 1.0 wt % genipin solution supplemented with 300 mg/L calcium phosphate at 0° C. for 2 weeks in a dark room. The solutions were replaced every 2 days. Then, the samples were further treated with vitamin E in supercritical $CO_2$ as mentioned above and then stored in vacuum bags and terminally irradiated to 25 kGy.

Mechanical Testing:

Samples were soaked in phosphate buffered saline (PBS) solution at room temperature for at least 30 minutes prior to mechanical testing. The bending test samples were notched to 1 mm depth and tested (Insight 2, MTS, Eden Prairie, Minn.) at a displacement rate of 10 mm/min. Fracture toughness and work-to-failure were calculated according to ASTM C1421-10. The IZOD impact test samples were also notched in the middle of the sample to 1 mm depth and tested according to ASTM F658-07 (CEAST 9050, Instron, Norwood, Mass.).

Reflectance Fourier Transform Infrared Spectroscopy (Reflectance-FTIR) of Bone Samples:

The bone samples were polished sequentially with 600 grit carbide papers for 3 minutes, 800 grit carbide papers for 3 minutes, and 1200 grit carbide paper for 3 minutes. Degree of collagen cross-linking was determined by specular reflection geometry at a resolution of 4 cm-1 as an average of 150 scans at every 200 um. Reflected IR light was gathered from bone surface at a near-normal angle. To analyze the reflectance spectrum, we used Kramers-Kronig relationship. Previously, it was shown that irradiation resulted in decrease in ratio of peak at 1660 $cm^{-1}$ to peak at 1690 $cm^{-1}$. Therefore, we used a similar method to quantify change in collagen cross-linking by taking the ratio of the peaks at (1660 $cm^{-1}$)/(1690 $cm^{-1}$).

Live-Dead and MTT Assay of Human Osteoblasts on Bone:

Terminally irradiated samples were cut into 4 mm×4 mm×1 mm and placed into a sterile 96 well plate. 60,000 osteoblasts in 20 uL DMEM media were added on top of each sample. The well plates were then incubated at 39.5° C. for 2 hours. Subsequent to incubation, 200 uL media was added to the wells containing the bone samples and incubated again at 39.5° C. for 24 hours. MTT assay (ThermoFisher, Vybrant®) was conducted as recommended by the manufacturer. Briefly, after the 24 hours incubation, samples and adherent cells were washed gently with PBS three times and then placed into a new sterile 96-well plate. 100 uL of media and then 10 uL MTT reagents were added to the samples. Samples were then incubated at 37° C. for 4 hours, and then 100 uL of stop solution was added into each well. After additional incubation at 37° C. for 4 hr, UV absorbance of the solution was measured at 570 nm.

Live dead assay (Life Technologies, Live/Dead® Cell Viability Assay) was conducted as recommended by the manufacturer. After the 24 hours incubation, 500 uL of assay reagent was added to completely cover the bone chips. Samples were then incubated for 24 minutes at 37° C. Samples were then washed gently with warm 37° C. PBS and then placed in a new 96 well plate. Samples were then imaged using a fluorescent microscope.

Statistical Analysis:

Statistical analysis was performed using a Student's t-test for one-way analysis of variance to compare more than two groups. Significance was assigned to $p<0.05$.

Figure 4A:
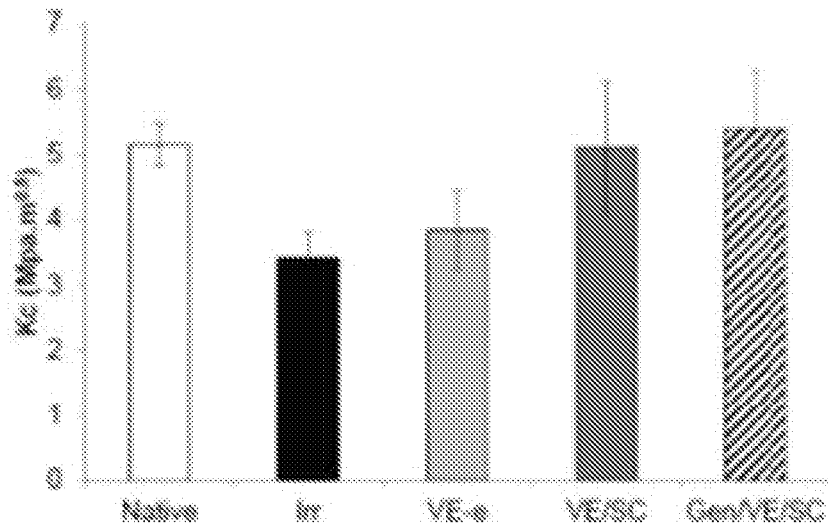
FIG. 4A shows the fracture toughness of bone samples doped with radioprotectant (Vitamin E) and radioprotectant and cross-linking agent (genipin). VE-e: vitamin E emulsion; VE/SC: vitamin E doping and supercritical carbon dioxide homogenization; Gen/VE/SC: genipin diffusion followed by vitamin E doping and supercritical carbon dioxide homogenization.
Figure 4B:
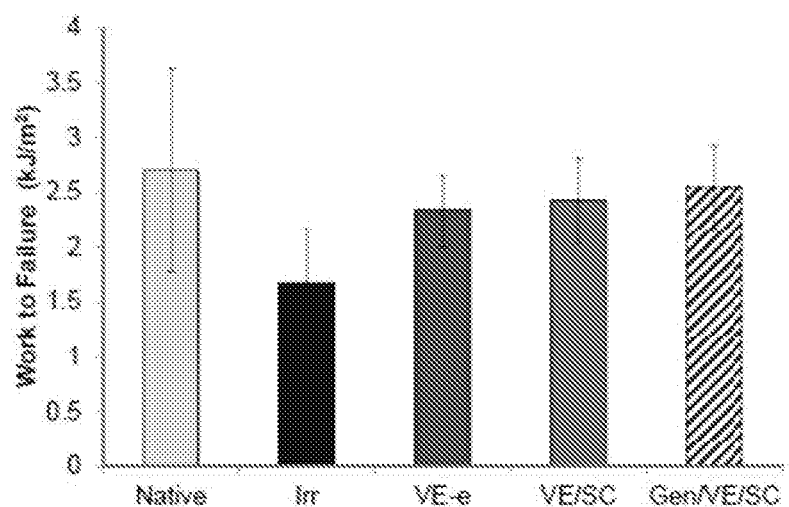
FIG. 4B shows the work to failure of bone samples doped with radioprotectant (Vitamin E) and radioprotectant and cross-linking agent (genipin). VE-e: vitamin E emulsion; VE/SC: vitamin E doping and supercritical carbon dioxide homogenization; Gen/VE/SC: genipin diffusion followed by vitamin E doping and supercritical carbon dioxide homogenization.

Irradiation of native bone grafts decreased their fracture toughness and work-to failure compared to native bone (34±2.7% and 74±8.1%, respectively; FIGS. 4A and 4B). The fracture toughness of samples doped using only an emulsion of the radioprotectant (vitamin E) showed a measurable but not statistically significant increase compared to the irradiated control (FIG. 3A). The fracture toughness of the sample doped in the pure antioxidant followed by supercritical homogenization (VE/SC) was comparable to that of unirradiated native control and higher than that of the irradiated control (p=0.0001, FIG. 4A). The work to failure of the sample doped with the radioprotectant using an emulsion (VE-e) and that of the sample doped with pure radioprotectant followed by supercritical carbon dioxide homogenization (VE/SC) were higher than that of the control irradiated without radioprotectant (p=0.0011 and 0.0001, FIG. 4B) and were comparable to that of unirradiated native bone (p>0.05, FIG. 4B).

Samples doped first with a cross-linking agent, then with the pure radioprotectant followed by supercritical homogenization (Gen/VE/SC) had statistically significant higher fracture toughness (FIG. 4A) and work to failure (FIG. 4B) compared to that of control irradiated without treatment. Both the fracture toughness and the work to failure of all of these samples were comparable to that of the unirradiated native bone (p>0.05) with complete recovery of fracture toughness and 84±9.8% recovery for the work to failure over control irradiated without treatment.

Figure 5A:
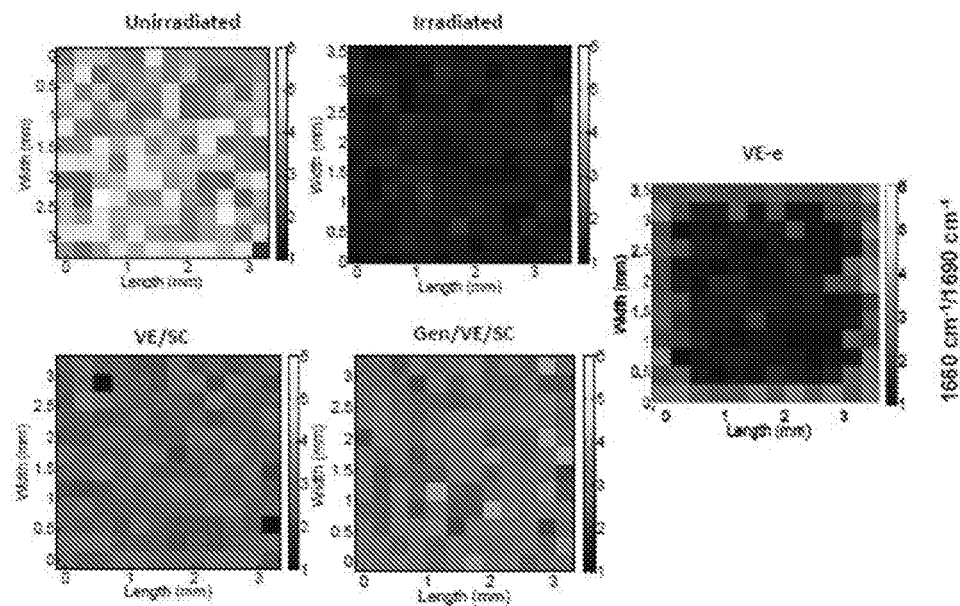
FIG. 5A shows representative maps of collagen cross-linking. Color map indicates cross-linking index (1660 $cm^{-1}$/1690 $cm^{-1}$).
Figure 5B:
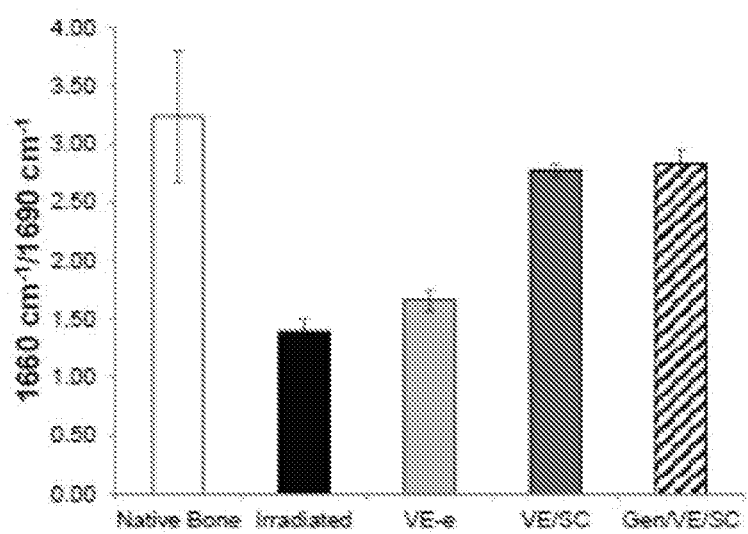
FIG. 5B shows mean collagen crosslinking index. VE-e: vitamin E emulsion; VE/SC: vitamin E doping and supercritical carbon dioxide homogenization; Gen/VE/SC: genipin diffusion followed by vitamin E doping and supercritical carbon dioxide homogenization.

Control irradiated without treatment showed low collagen crosslinking index (1660 $cm^{-1}$/1690 $cm^{-1}$) throughout the sample (FIG. 5A). Samples doped with vitamin E emulsion had higher crosslinking index along the outer edge of the samples than the center of the samples (FIG. 5A). Samples doped with vitamin E followed by supercritical carbon dioxide homogenization (VE/SC) and samples doped with genipin, then vitamin E by this method (Gen/VE/SC) showed higher cross-linking index throughout the samples compared to that of control irradiated without treatment (FIG. 5A). The mean crosslinking index of all treated samples was higher (14±1.4%, 74±2.8% and 78±6.7%, respectively) than that of control irradiated without treatment (p=0.015, 0.0001 and 0.001 respectively; FIG. 5B) and except for the VE-e, was comparable to that of unirradiated native bone (p>0.05).

Figure 6A:
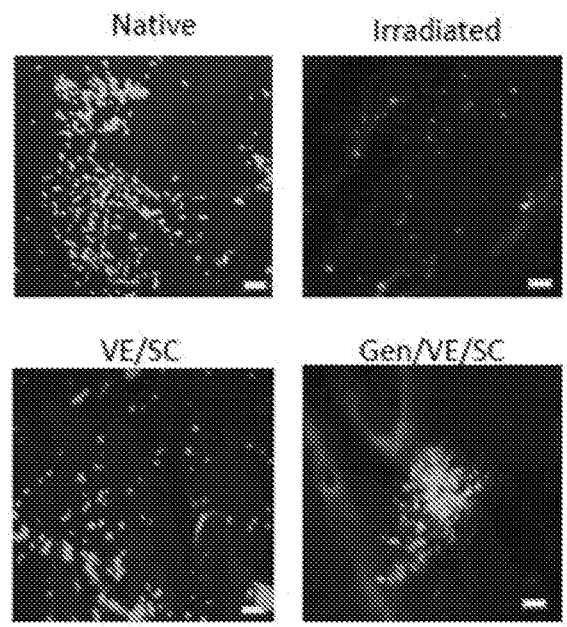
FIG. 6A shows a qualitative assessment of osteoblast attachment by staining for live and dead cells on control and treated surfaces. The scale bar represents 100 µm.
Figure 6B:
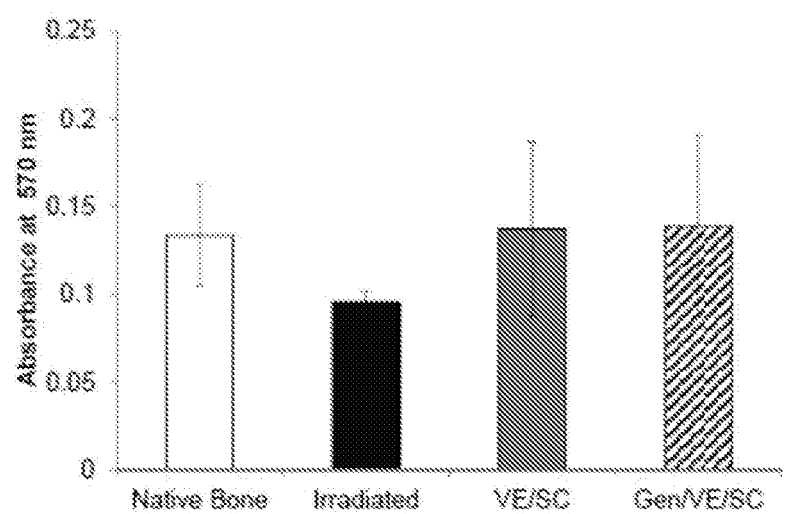
FIG. 6B shows a quantitative assessment of osteoblast attachment by detachment and reaction of adherent cells on control and treated surfaces with the MTT assay. VE-e: vitamin E emulsion; VE/SC: vitamin E doping and supercritical carbon dioxide homogenization; Gen/VE/SC: genipin diffusion followed by vitamin E doping and supercritical carbon dioxide homogenization.

Osteoblast (both live and dead) attachment on the surfaces of control bone irradiated without treatment was less than that measured on untreated (native) bone surfaces. Samples doped with vitamin E as radioprotectant followed by supercritical carbon dioxide homogenization (VE/SC) had similar amount of adherent live and dead osteoblasts as that measured on the surfaces of unirradiated native bone. Doping with genipin and vitamin E before sterilization caused the cells to cluster closely together on these surfaces (FIG. 6A). There was statistically significant decrease in the MTT absorbance from cells attached on the surfaces of control samples irradiated without treatment compared to that measured on the surfaces of native bone (FIG. 6B). There was no statistically significant difference between the MTT absorbance from cells attached to native bone surfaces and surfaces doped with vitamin E or vitamin E/genipin (p>0.05).

Minimal compromise in mechanical strength, osteoinduction, and osteoconduction of cortical allografts is crucial for repair of fractures, bone replacement during tumor removal, and reconstruction of skeletal defects. Sterilization through ionizing radiation is desirable to ensure deactivation of all unwanted bacteria and virus such as HIV that might accidentally be transmitted from the donor to the allograft recipient. However, the incidence of in vivo fracture of human cortical grafts is higher when allografts sterilized with ionizing radiation are used, suggesting that the mechanical properties of irradiated bone allograft need to be improved for efficient use of this method for sterilization.

The biocompatible free radical scavenger vitamin E can be used as a radioprotectant in bone allograft to minimize the adverse effects of gamma sterilization. Vitamin E is a hindered phenol chain breaking antioxidant, which can act very efficiently to scavenge free radicals caused by reactive oxygen species and protect cell membrane lipids against oxidation.

The diffusion of additives into cortical bone is severely limited due to the low diffusion coefficients of compounds through this dense structure.

Treatment of bone allografts with vitamin E doping followed by supercritical fluid homogenization before radiation sterilization (VE/SC) completely preserved the fracture toughness and work to failure of unirradiated, native bone (FIGS. 4A and 4B). This method was superior in preserving the fracture toughness over bone treated with vitamin E emulsions, presumably because the maximum concentration of vitamin E used in the emulsion technique (15 mg/mL) resulted in lower concentration of the radioprotectant in the bone. By contacting the bone with pure radioprotectant, a high surface concentration could be achieved, which could then be homogenized through the bone by the diffusion of the supercritical carbon dioxide. An additional benefit was the decreased diffusion time, which resulted in a total processing time of 30 hours compared to 2 weeks by the emulsion method with similarly sized samples. In fact, the higher collagen cross-linking around the edges of the samples treated by the vitamin E emulsion (FIG. 5A) suggested that 2 weeks were not sufficient to drive the vitamin E throughout the components when using an emulsion.

Bone doped with vitamin E and homogenized by supercritical $CO_2$ (VE/SC) were superior in preserving the fracture toughness of the native bone when compared to samples treated using a vitamin E emulsion (VE-e) (FIG. 4A). This was most likely due to more homogeneous distribution of antioxidants through supercritical treatment as shown with higher overall crosslinking index throughout the samples (FIGS. 5A and 5B). More importantly, the homogeneous distribution of the radioprotectant obtained using this technique resulted in the fracture toughness of native bone being completely preserved when sterilized at 25 kGy (FIG. 4A).

It was important to assess that doping of radioprotectant and the subsequent supercritical fluid treatment did not hinder osteoblast attachment to the bone allograft surfaces. Qualitative analysis of live-dead assay stained surfaces and quantitative analysis of the number of osteoblasts attached to the surfaces revealed that irradiation without treatment significantly decreased the ability of osteoblasts to attach to the bone surfaces (FIGS. 6A and 6B); therefore, it is likely that radiation sterilization alone compromises not only the mechanical strength but also the integration of the graft with host bone. In contrast, doping with radioprotectant followed by supercritical carbon dioxide before irradiation did not affect the ability of osteoblast attachment on the bone surfaces; the osteoblasts on these surfaces were not only comparable in number to those attached to the unirradiated, native bone surfaces but also showed similar density and dispersion characteristics (FIGS. 6A and 6B). This suggests that the use of vitamin E as radioprotectant incorporated using this technique to homogeneously distribute the radioprotectant can improve the integration of the irradiated allograft with host bone.

Based on the knowledge that the disruption of the collagen network via chain scissioning during irradiation is the major mechanism behind the loss of the mechanical properties of bone allografts, we hypothesized that additional cross-linking of collagen may be advantageous. We proposed the addition of a cross-linking agent would increase collagen cross-linking after irradiation and further improve the mechanical strength of the treated bone allografts after radiation sterilization. Our hypothesis tested negative presumably because vitamin E was very effective in protecting the collagen structure and additional cross-linking, if any, did not result in further improvement of properties (FIGS. 4A and 4B). While there was not a clear benefit of the additional cross-linking agent in this system, the use of additional cross-linker may be used to provide benefit in conjunction with radioprotectants and radioprotectant incorporation methods which may not protect collagen to the fullest extent.

The amount of time for diffusion of vitamin E into bone by traditional methods was largely decreased; improving the feasibility of using such a method in the processing of structural grafts. The processing of other types of grafts such as cortical or cancellous chips is easily possible with this method, where processing times would be further reduced due to the small effective diffusion length required for these smaller samples.

Example 2

Live-Dead Imaging of Bacterial Growth from Spore Infused Bone Allografts

The diaphysis of the bovine tibia was machined into 10 mm×10 mm×3.7 mm blocks. All samples were then washed with isopropanol for 2 hours and then delipidated in 1:1 chloroform:methanol for 48 hours. Samples were then divided into three main groups: control-unirradiated, control-irradiated, and VE/SC irradiated.

Samples in the VE/SC group were immersed in pure vitamin E at 55° C. for 6 hours. Samples were then homogenized in supercritical $CO_2$ fluid at 40° C. and 85 bar for 24 hours. All samples were then immersed in the 1:10 diluted *Bacillus subtilis* (*B. subtilis*) spore solution (110649, EMD Millipore) for 48 hours at 4° C. After removing excess liquid, all samples were separately packaged in vacuum bags. All samples except those in the control-unirradiated groups were irradiated using an electron beam to 25 kGy.

To assess the sterility of the samples, all samples were aseptically transferred to sterile 12-well plates. Two milliliters of Trypsin-soy broth was added to each good plate and subsequently incubated for 24 hours at 37° C. The growth of bacteria on the bone was imaged using Live/Dead bacterial viability kit (L7012, ThermoFisher Scientific).

Figure 7:
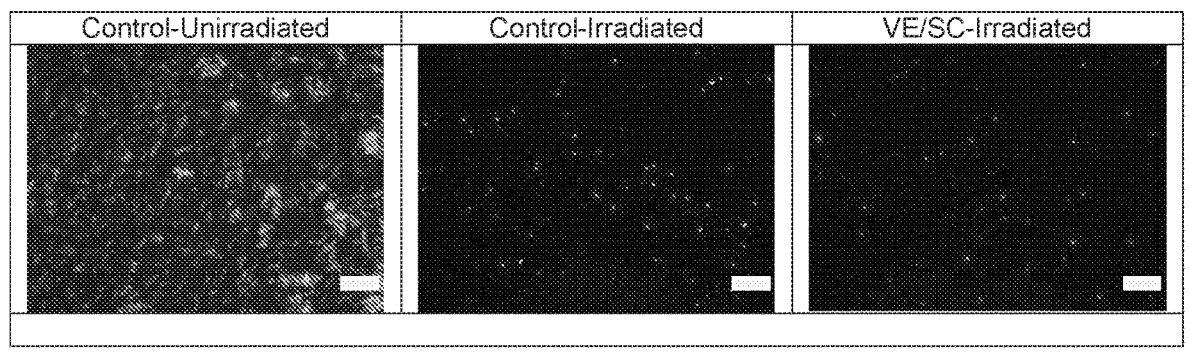
FIG. 7 shows Live/Dead imaging of the *B. subtilis* on the spore-infused allografts. Green and red rods indicate live and dead bacteria respectively. Spheres indicate non-proliferating spores. Scale bar=10 µm.

Green-stained *bacillus* structures were observed in the control-unirradiated samples but not in the control-irradiated and VE/SC-irradiated samples (FIG. 7). Only spherical structures were observed in the control-irradiated and VE/SC-irradiated samples, indicating the presence of only non-proliferating spores. This result indicated that treatment with VE/SC did not compromise the ability of irradiation to eradicate bacterial spores.

Example 3

Quantification of B. *Subtilis* Proliferation from Spore Infused Irradiated Bone Allografts Three groups of spore infused bone allografts (control-unirradiated, control-irradiated, and VE/SC-irradiated) were prepared as mentioned in Example 2. To assess the sterility of the samples, all samples were aseptically transferred to sterile 12-well plates. Two milliliters of Trypsin-soy broth was added to each well plate and subsequently incubated for 24 hours at 37° C. Samples were then sonicated in the original broth to detach any bone-adherent bacteria. Bacteria in the supernatant was then quantified by measuring absorbance at 600 nm (OD 600).

Figure 8:
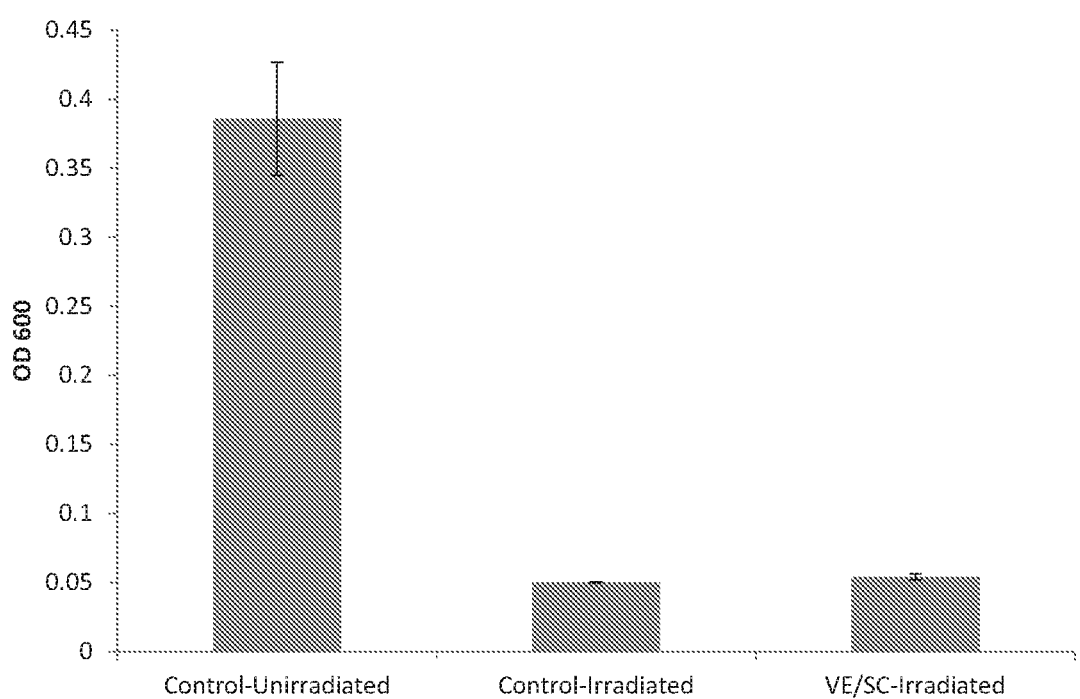
FIG. 8 shows *B. subtilis* concentration in the media after 24 hours incubation for control-unirradiated, control-irradiated, and VE/SC-irradiated bone that has been immersed in *B. subtilis* spore for 48 hours prior to terminal irradiation.

The OD600 of control-unirradiated samples was significantly higher than the OD600 of control-irradiated and VE/SC-Irradiated samples (FIG. 8). There was no statistically significant difference in OD600 between irradiated and VE/SC (FIG. 8). This result indicated that treatment with VE/SC did not compromise the ability of irradiation to eradicate bacterial spores.

Example 4

Confocal Imaging of Mouse Osteoclast Cultures on Bone Allograft

Three types of bone allografts were tested in this experiment: Unirradiated sterile bone allograft (control-unirradiated), irradiated sterile bone allograft (control-irradiated), and VE/SC-irradiated allografts prepared as described in Example 2.

Murine monocyte/macrophages (RAW264.7, ATCC) was differentiated into osteoclast according to the protocol developed by Itou et al. (Arteriosclerosis, *Thrombosis, and Vascular Biology*, 2013. 113: p. 302576). The cells were seeded onto the surface of the bone sample (5000 cells/sample) and incubated in 10% FBS in minimum essential medium eagle α-modified media (α-MEM, Sigma-Aldrich), supplemented with penicillin and streptomycin, and 100 ng/mL recombinant mouse RANKL (R&D Systems) for 3 days. Incubation was performed in a static condition in air at 37° C., 5% $CO_2$, and high humidity. Three stains were applied to the resulting bone-adherent osteoclasts: Tartrate-resistant acid-phosphatase stain (TRAP), actin stain, and cell nuclei stain.

Fluorescence-based staining for TRAP in osteoclast was performed according to the protocol developed by Filgueira et al. (*J Bone Mineral Research*, 1992. 7(6): p. 683-693). The staining solution was composed of 200-µM ELF97 (Sigma-Aldrich), 110 mM acetate buffer (pH 5.2), 1.1 mM sodium nitrite, and 7.4 mM tartrate. After cells on the surface of bone were fixed with 4% formaldehyde in PBS for 30 minutes, 1 ml of the staining solution was added to the bone and incubated in the dark for 15 minutes.

Actin was stained with phallotoxins dye (Alexa Fluor®594 Phalloidin, Thermo Fisher Scientific) according to the manufacturer's recommended protocol. Briefly, cells adherent on the bone samples were washed twice with 37° C. phosphate-buffered saline, pH 7.4. The samples were then fixed with 3.7% formaldehyde solution in PBS for 10 minutes. After washing with PBS two more times, samples were immersed in 0.1% Triton X-100 in PBS for 5 minutes. After washing again for two more times with PBS, diluted fluorescent phallotoxins solution was added to the bone samples (25 µL stock solution in 1000 µL PBS containing 1% bovine serum albumin).

Cell nuclei were stained with 300 nM solution of 4',6-diamidino-2-phenylindole solution (DAPI, Sigma-Aldrich, St. Louis, Mo.) in PBS. Staining was conducted for 5 minutes in the dark. Samples were then washed with PBS for two times. Samples were imaged using confocal fluorescence microscope (LSM 880, Zeiss, Germany).

Figure 9:
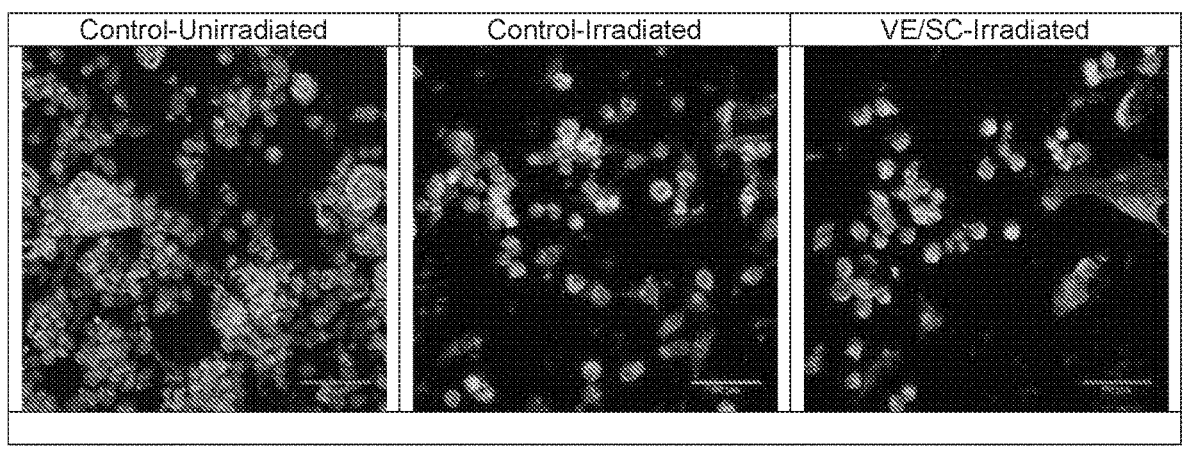
FIG. 9 shows confocal fluorescence imaging of osteoclast grown on the surface of bone allograft. Green=TRAP, red=actin, blue=nucleus. Scale bar=50 µm.

Control-unirradiated samples showed the highest cell density as compared to control-irradiated and VE/SC-irradiated samples (FIG. 9). Multinucleated cells (terminally differentiated osteoclast) could be observed in both control-unirradiated and VE/SC-irradiated samples. No multinucleated osteoclasts could be observed in control-irradiated samples.

Example 5

Confocal Imaging of Mouse Osteoblast Cultures on Bone Allograft

Three types of bone allografts were tested in this experiment: Unirradiated sterile bone allograft (control-unirradiated), irradiated sterile bone allograft (control-irradiated), and VE/SC-irradiated allografts prepared as described in Example 2.

Murine osteoblastic cell line (MC3T3-E1 Subclone 4, ATCC CRL-2593) were cultured according to the protocol suggested by ATCC. MC3T3-E1 osteoblast was cultured in alpha minimum essential medium (α-MEM) supplemented with 10% fetal bovine serum (FBS) for 2 days. The cell layer was then exposed to 0.25% (w/v) Trypsin in 0.52 mM EDTA solution to remove all traces of trypsin inhibitor. Three ml of the trypsin-EDTA solution was then added for 15 minutes to detach the cell from the culture flask. The cells were then resuspended in α-MEM and 5,000 cells were added to the bone samples and incubated in air at 37° C., 5% $CO_2$, and high humidity (Smith et al., *International Journal of Nanomedicine*, 2006. 1(2): p. 189-194). The media was replenished every 2 days and was cultured for a total of 6 days. Three stains were applied to the resulting bone-adherent osteoblasts: alkaline phosphatase (ALP) stain, actin stain, and cell nuclei stain.

Alkaline phosphatase was stained with fluorescent alkaline phosphatase substrate (Vector® Red, Vector Laboratories, Burlingame, Calif., USA) according to the manufacturer's recommended protocol. Briefly, staining solution was prepared by adding 80 μl of reagent 1, 80 μl of reagent 2, and 80 μl of reagent 3 to 5 ml of 100 mM Tris-HCl, 0.1% Tween 20 buffer, pH 8.2-8.5. Working solution (1 ml) was added to the bone samples and incubated for 40 minutes in the dark. Samples were then washed with PBS.

Actin was stained with phallotoxins dye (Alexa Fluor®594 Phalloidin, Thermo Fisher Scientific) according to the manufacturer's recommended protocol. Briefly, cells adherent on the bone samples were washed twice with 37° C. phosphate-buffered saline, pH 7.4. The samples were then fixed with 3.7% formaldehyde solution in PBS for 10 minutes. After washing with PBS two more times, samples were immersed in 0.1% Triton X-100 in PBS for 5 minutes. After washing again for two more times with PBS, diluted fluorescent phallotoxins solution was added to the bone samples (25 μL stock solution in 1000 μL PBS containing 1% bovine serum albumin).

Cell nuclei were stained with 300 nM solution of 4',6-diamidino-2-phenylindole solution (DAPI, Sigma-Aldrich, St. Louis, Mo.) in PBS. Staining was conducted for 5 minutes in the dark. Samples were then washed with PBS for two times.

Figure 10:
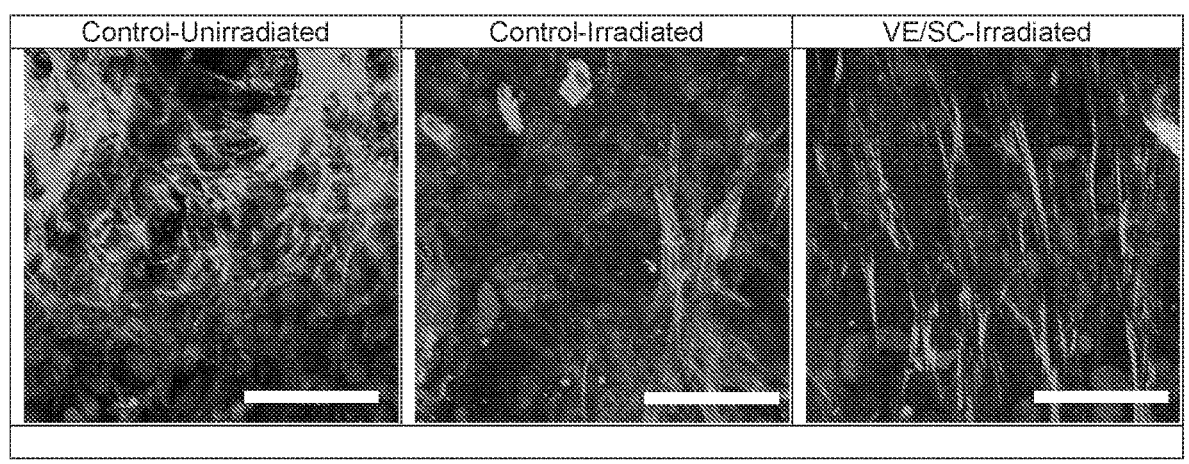
FIG. 10 shows confocal fluorescence imaging of osteoblast grown on the surface of bone allograft. Green=actin, red=ALP, blue=nucleus. Scale bar=100 µm.

Control-unirradiated samples had higher cell density than both control-irradiated and VE/SC-irradiated. There was no apparent difference in cell density between control-irradiated and VE/SC irradiated samples. Alkaline phosphatase products (red, FIG. 10) could be detected in all samples.

Example 6

Viability Quantification of Osteoclast Adherent on Bone Allograft

Three types of bone allografts are tested in this experiment: Unirradiated sterile bone allograft (control-unirradiated), irradiated sterile bone allograft (control-irradiated), and VE/SC-irradiated allografts prepared as described in Example 2.

Murine monocyte/macrophages (RAW264.7, ATCC) was differentiated into osteoclast according to the protocol developed by Itou et al. (Arteriosclerosis, *Thrombosis, and Vascular Biology*, 2013. 113: p. 302576). The cells were seeded onto the surface of the bone sample (5000 cells/sample) and incubated in 10% FBS in minimum essential medium eagle α-modified media (α-MEM, Sigma-Aldrich), supplemented with penicillin and streptomycin, and 100 ng/mL recombinant mouse RANKL (R&D Systems) for 3 days. Incubation was performed in a static condition in air at 37° C., 5% $CO_2$, and high humidity. Three stains were applied to the resulting bone-adherent osteoclasts: Tartrate-resistant acid-phosphatase stain (TRAP), actin stain, and cell nuclei stain.

Cell viability was measured using a Cell Counting Kit-8 (CCK-8) (Dojindo Molecular Technologies, Gaithersburg, Md.) according to the manufacturer's instructions. Briefly, the media where the bone samples were incubated in were removed and 100 μl of the CCK-8 solution and 900 μl PBS was added to each well. The plates were incubated at 37° C. for 1 h, after which the optical density (OD) was measured at 450 nm on a microplate reader. The results were presented as the percentage of viable cells over control.

Figure 11:
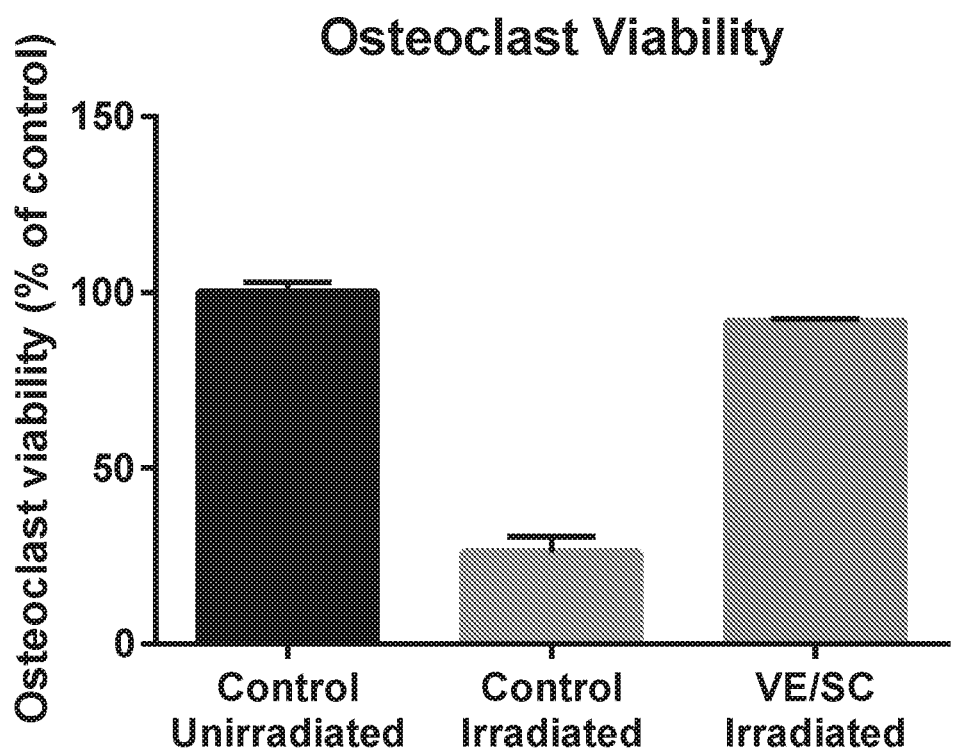
FIG. 11 shows relative osteoclast viability (relative to the mean of control-unirradiated samples). Data are presented as mean±s.d. (n=6 per group).

Control-irradiated samples significantly had less viable adherent cells on their surfaces than that on the control-unirradiated and VE/SC-irradiated allografts' surfaces (FIG. 11, $p<0.0001$). There was no statistically significant difference in cell viability between the control-unirradiated and VE/SC-irradiated allografts (FIG. 11).

Example 7

Viability Quantification of Osteoblast Adherent on Bone Allograft

Three types of bone allografts are tested in this experiment: Unirradiated sterile bone allograft (control-unirradiated), irradiated sterile bone allograft (control-irradiated), and VE/SC-irradiated allografts prepared as described in Example 2.

Murine osteoblastic cell line (MC3T3-E1 Subclone 4, ATCC CRL-2593) were cultured according to the protocol suggested by ATCC. MC3T3-E1 osteoblast was cultured in alpha minimum essential medium (α-MEM) supplemented with 10% fetal bovine serum (FBS) for 2 days. The cell layer was then exposed to 0.25% (w/v) Trypsin in 0.52 mM EDTA solution to remove all traces of trypsin inhibitor. Three milliliters (ml) of the trypsin-EDTA solution was then added for 15 minutes to detach the cell from culture flask. The cells were then resuspended in α-MEM and 5,000 cells were added to the bone samples and incubated in air at 37° C., 5% $CO_2$, and high humidity (Smith et al., *International Journal of Nanomedicine*, 2006. 1(2): p. 189-194). The media was replenished every 2 days and was cultured for a total of 6 days. Three stains were applied to the resulting bone-adherent osteoblasts: alkaline phosphatase (ALP) stain, actin stain, and cell nuclei stain.

Cell viability was measured using a Cell Counting Kit-8 (CCK-8) (Dojindo Molecular Technologies, Gaithersburg, Md.) according to the manufacturer's instructions. Briefly, the media where the bone samples were incubated in were removed and 100 µl of the CCK-8 solution and 900 µl PBS was added to each well. The plates were incubated at 37° C. for 1 h, after which the optical density (OD) was measured at 450 nm on a microplate reader. The results were presented as the percentage of viable cells over control.

Figure 12:
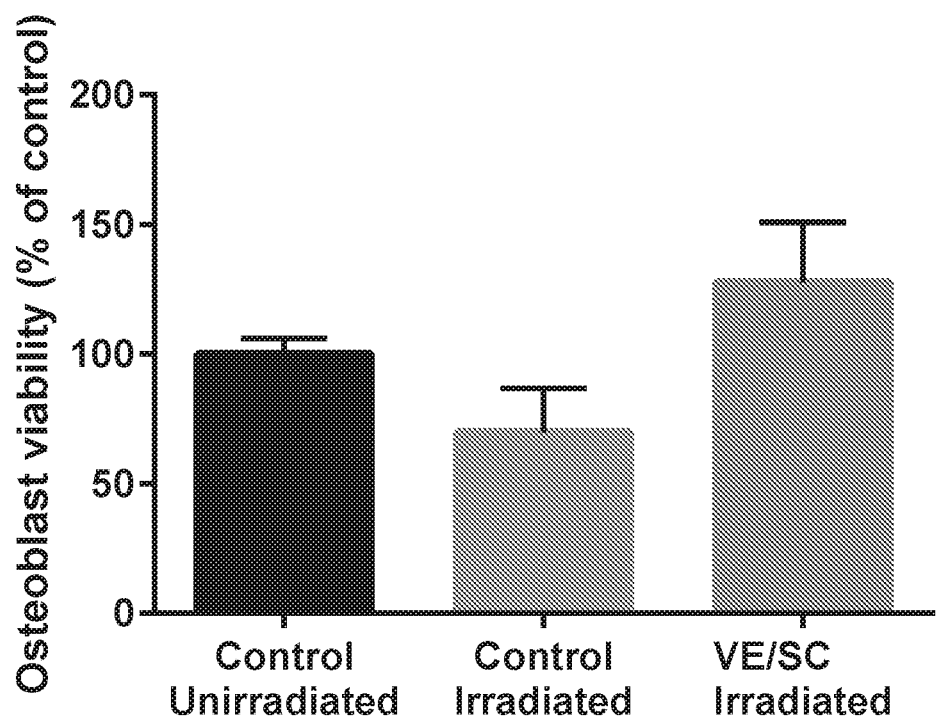
FIG. 12 shows relative osteoblast viability (relative to the mean of control-unirradiated samples). Data are presented as mean±s.d. (n=6 per group).

Control-irradiated samples significantly had less viable adherent cells on its surface than that of the control-unirradiated and VE/SC-irradiated allografts (FIG. 12, p<0.005). The osteoblast viability of the VE/SC irradiated samples were statistically significantly higher than that of the control unirradiated samples (FIG. 12, p<0.05).

Example 8

Alkaline Phosphatase Activity Quantification of Osteoblast Adherent on Bone Allograft Three types of bone allografts are tested in this experiment: Unirradiated sterile bone allograft (control-unirradiated), irradiated sterile bone allograft (control-irradiated), and VE/SC-irradiated allografts prepared as described in Example 2.

Murine osteoblastic cell line (MC3T3-E1 Subclone 4, ATCC CRL-2593) were cultured according to the protocol suggested by ATCC. MC3T3-E1 osteoblasts were cultured in alpha minimum essential medium (α-MEM) supplemented with 10% fetal bovine serum (FBS) for 2 days. The cell layer was then exposed to 0.25% (w/v) Trypsin in 0.52 mM EDTA solution to remove all traces of trypsin inhibitor. Three milliliters (ml) of the trypsin-EDTA solution was then added for 15 minutes to detach the cell from culture flask. The cells were then resuspended in α-MEM and 5,000 cells were added to the bone samples and incubated in air at 37° C., 5% $CO_2$, and high humidity (Smith et al., *International Journal of Nanomedicine*, 2006. 1(2): p. 189-194). The media was replenished every 2 days and was cultured for a total of 6 days. Three stains were applied to the resulting bone-adherent osteoblasts: alkaline phosphatase (ALP) stain, actin stain, and cell nuclei stain.

Alkaline phosphatase activity was measured using colorimetric alkaline phosphatase assay kit (ab83369, Abcam) according to the manufacturer's recommended protocol. Bone samples were removed from the medium and washed twice with PBS. Cells adherent to the bone samples were lyzed by submerging into 1 ml of 1% Triton 100× solution. Resulting suspension was centrifuged at 4° C. for 15 minutes to remove any insoluble material. 0.5 ml p-nitro phenyl phosphate (p-NPP) solution was then added to the supernatant and incubated for 45 minutes at room temperature. The p-NPP solution is composed of 100 µl of p-NPP concentrate per 2 ml of 100 mM sodium bicarbonate/carbonate buffer, pH 10. The absorbance of the mixture was read at 405 nm. ALP activity per number of cells was calculated by taking the ratio of the mean of the total alkaline phosphatase activity to mean the total number of cells adherent to the bone as calculated in Example 5.

Figure 13A:
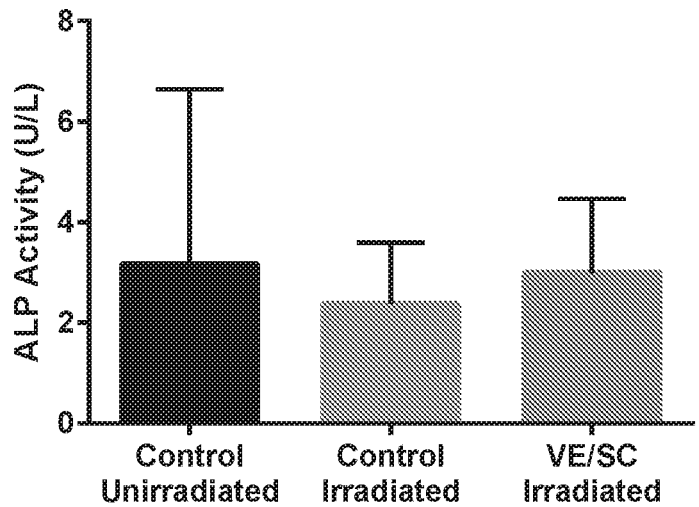
FIG. 13A shows total alkaline phosphatase activity and ALP activity per number of cells. ALP activity per number of cells was calculated by taking the ratio of the mean of the total alkaline phosphatase activity to mean the total number of cells adherent to the bone.
Figure 13B:
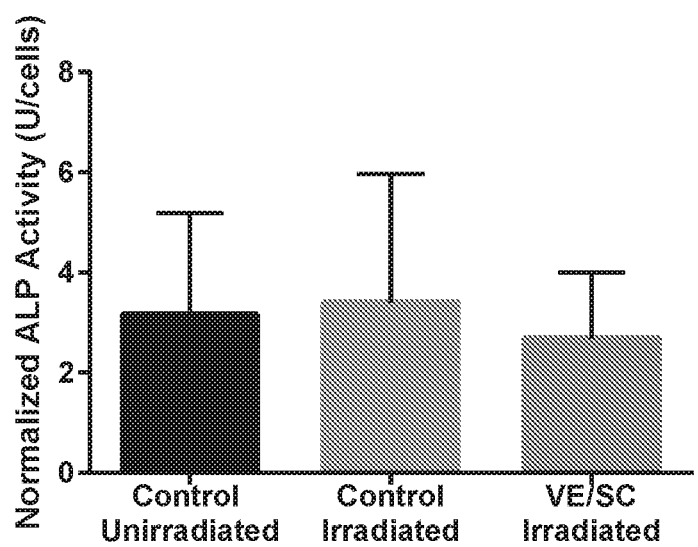
FIG. 13B shows total alkaline phosphatase activity of osteoblasts adherent to the bone allograft.
Figures 14A, 14B:
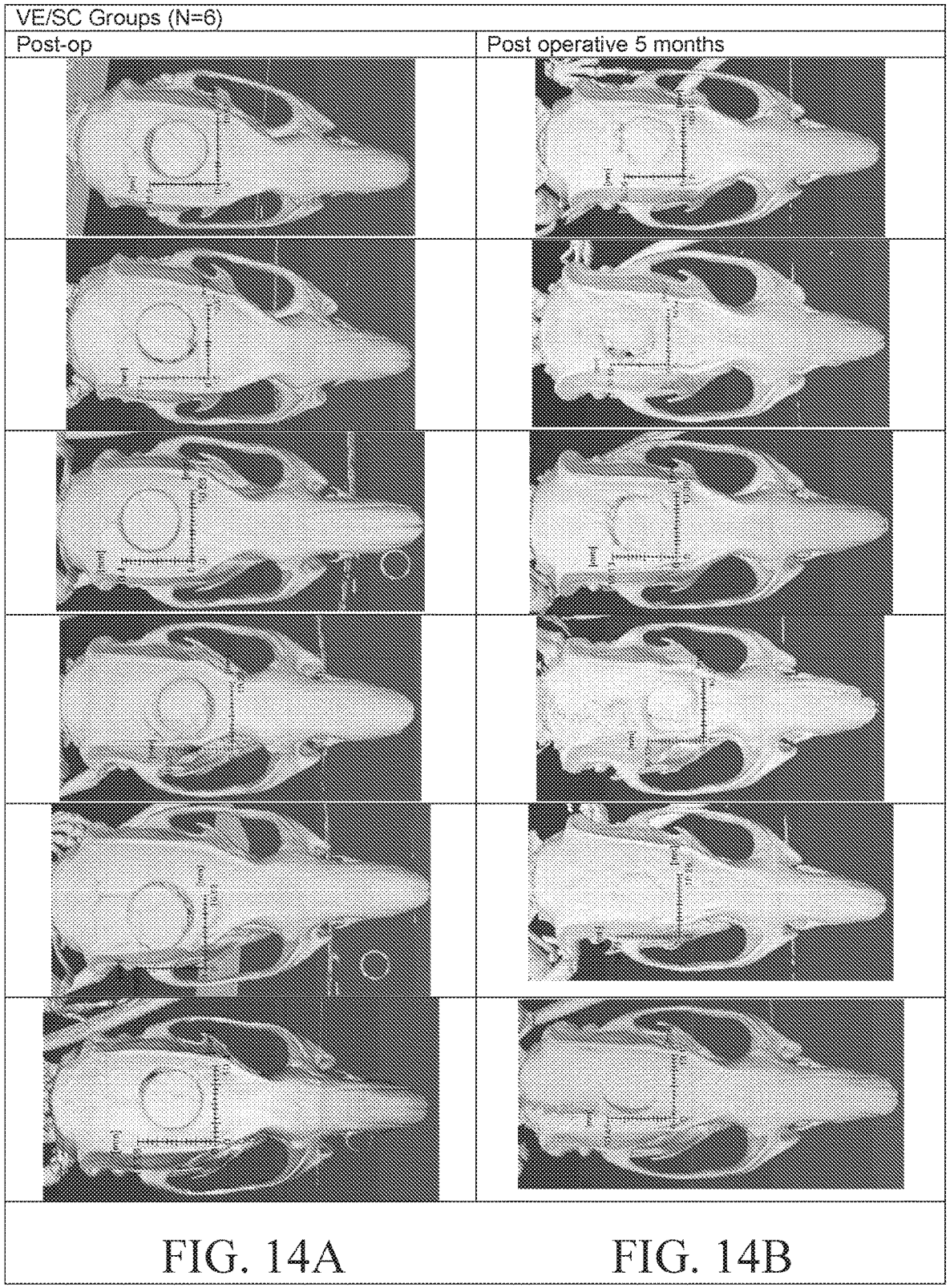
FIG. 14A shows the progression of bone regeneration in rats receiving VE/SC irradiated allografts as monitored by in vivo computerized tomography (CT) immediately after surgery (left column).
FIG. 14B shows the progression of bone regeneration in rats receiving VE/SC irradiated allografts as monitored by in vivo CT for the corresponding samples of FIG. 14A five months after surgery (right column).
Figures 15A, 15B:
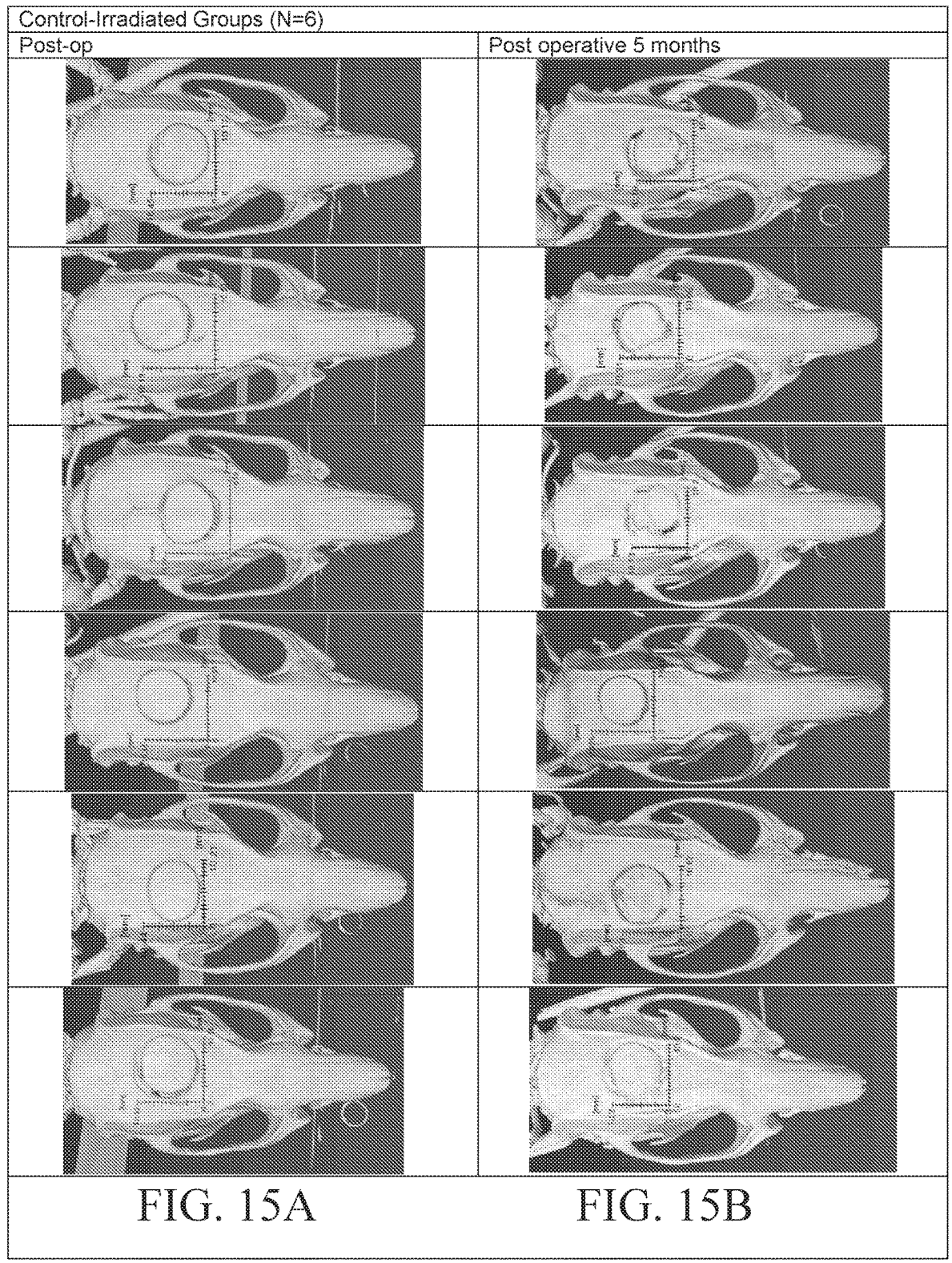
FIG. 15A shows the progression of bone regeneration in rats receiving Control-irradiated allografts as monitored by in vivo CT immediately after surgery.
FIG. 15B shows the progression of bone regeneration in rats receiving Control-irradiated allografts as monitored by in vivo CT for the corresponding samples of FIG. 15A five months after surgery.

No statistically significant difference was observed in total ALP activity and ALP activity per number of cells for all three groups (FIGS. 13A and 13B).

Example 9

In Vivo Murine Calvaria Bone Regeneration Model

The in vivo murine calvaria bone regeneration model consisted of two main steps: allograft extraction from rat calvaria and subsequent implantation of processed allografts into other rats.

For allograft extraction, twelve Sprague-Dawley rats aged 8 weeks were euthanized using $CO_2$, and the rat calvaria was carefully isolated. Using a 8 mm trephine saw, a circular allograft was obtained from the mid-parietal bone along the sagittal suture. Allografts were then washed with isopropanol for 2 hours and then delipidated in 1:1 chloroform: methanol for 48 hours. Samples were then dried at 25° C. in the dark for 24 hours. The twelve allografts were then randomized into two groups: a control group and the VE/SC group. Allografts in the VE/SC group were immersed in vitamin E at 55° C. for 6 hours, then treated in supercritical $CO_2$ at 40° C. and 85 bars for 24 hours. Both samples in the control and VE/SC groups were packaged in vacuum bags and irradiated to 25 kGy.

Implantation of the allograft into rats using critical size calvarial defect was adapted from Spicer et al. (*Nature Protocols*, 2012. 7: p. 1918-1929). Twelve Sprague-Dawley rats aged 8 weeks were randomly assigned to either control (sterilized allograft) or VE/SC allografts (sterilized).

Anesthesia was achieved using inhaled isoflurane (2%) supplemented with oxygen (1.2 liters/min). Pre-emptive analgesia was administered before the procedure started (buprenorphine 0.05 mg/kg). No pre or postoperative antibiotics were administered. Around 1.5 cm incision down to the periosteum was made along the middle sagittal crest over the scalp. After pushing the periosteum laterally, 8 mm diameter calvarial defect was created using trephine drill. The circular bone inside the defect was removed and was replaced with either sterile control allograft or sterile VE/SC allograft. The periosteum was then closed over the implant using 4-0 Monocryl sutures. The skin was then closed over the periosteum using 3-0 plain gut suture.

In vivo computed tomography was performed immediately after surgery and every four weeks until five months. The rats were anesthetized using inhaled isoflurane (2%) supplemented with oxygen (1.2 liters/min) throughout the computed tomography scan (10 minutes). The computed tomography was performed using high-resolution CT (Inveon, Siemens), acquired with 80 kVp and 500 µA X-ray power, 256 projections, and 180 µm isotropic resolution.

As compared to the rats receiving control-irradiated allografts, rats receiving VE/SC-irradiated allografts showed faster bone regeneration and integration between the allograft and naïve bone as indicated by the absence of lucencies between the native bone and allograft at 5 months after implantation (FIGS. 14A, 14B, 15A and 15B). These results suggested that the incorporation of vitamin E into bone allograft prior to radiation sterilization enhanced the integration of processed allograft to host bone.

Thus, the invention provides systems and methods of protecting allograft against radiation damage. The invention also provides systems and methods of incorporating additives such as radioprotectants into allograft tissue.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the embodiments contained herein.

What is claimed is:

1. A method of making a radiation sterilized allograft, the method comprising:
   a. providing an allograft;
   b. cleaning the allograft;
   c. contacting the allograft with at least one radioprotectant(s), thereby obtaining a radioprotectant-doped allograft;
   d. contacting the radioprotectant-doped allograft with a supercritical fluid to improve spatial uniformity of a concentration profile of the radioprotectant(s) within the allograft resulting in a homogenized radioprotectant doped allograft; and
   e. irradiating the homogenized radioprotectant doped allograft, thereby obtaining a radiation sterilized allograft.

2. The method according to claim 1, wherein the allograft is a bone allograft.

3. The method according to claim 2, wherein the bone allograft is cancellous or cortical.

4. The method according to claim 2, wherein the bone allograft is crushed, machined or whole.

5. The method according to claim 1, wherein the contact with the radioprotectant is done when the radioprotectant is in pure form, dissolved in a solvent or solution, or is in emulsified form in a solution, gas, fluid or solid.

6. The method according to claim 1, wherein the allograft is contacted with the radioprotectant at a temperature between room temperature and 60° C.

7. The method according to claim 1, wherein the supercritical fluid is carbon dioxide.

8. The method according to claim 1, wherein the radioprotectant-doped allograft is contacted with the supercritical fluid at a temperature between room temperature and 100° C.

9. The method according to claim 1, wherein the radioprotectant-doped allograft is contacted with the supercritical fluid for a time between 4 and 24 hours.

10. The method according to claim 1, wherein a terminal irradiation dose is below 30 kGy.

11. The method according to claim 1, wherein a terminal irradiation dose is between 30 and 50 kGy.

12. A method according to claim 1, wherein a terminal irradiation dose is above 50 kGy.

13. A method of making a radiation sterilized allograft, the method comprising:
   a. providing an allograft;
   b. cleaning allograft;
   c. contacting allograft with radioprotectant(s) and at least one more additive, thereby obtaining a radioprotectant-doped allograft;
   d. contacting the radioprotectant-doped allograft with a supercritical fluid to improve spatial uniformity of a concentration profile of the radioprotectant(s) within the allograft resulting in a homogenized radioprotectant doped allograft; and
   e. irradiating the homogenized radioprotectant doped allograft.

14. The method of claim 13, wherein the allograft is a bone allograft.

15. The method according to claim 14, wherein the bone allograft is cancellous or cortical.

16. The method according to claim 15, wherein the bone allograft is crushed, machined or whole.

17. The method of claim 13, wherein the contact with the radioprotectant is done when the radioprotectant is in pure form, dissolved in a solvent or solution, or is in emulsified form in a solution, gas, fluid or solid.

18. The method of claim 13, wherein the allograft is contacted with radioprotectant at a temperature between room temperature and 60° C.

19. The method of claim 13, wherein the supercritical fluid is carbon dioxide.

20. The method of claim 13, wherein the radioprotectant-doped allograft is contacted with supercritical fluid at a temperature between room temperature and 100° C.

21. The method of claim 13, wherein the radioprotectant-doped allograft is contacted with supercritical fluid for a time between 4 and 24 hours.

22. The method of claim 13, wherein a terminal irradiation dose is below 30 kGy.

23. The method of claim 13, wherein a terminal irradiation dose is between 30 and 50 kGy.

24. The method of claim 13, wherein a terminal irradiation dose is above 50 kGy.

25. A material for repairing a bone defect, the material comprising: a radioprotectant-doped allograft created by the method of claim 1.

26. The material of claim 25, wherein the allograft is a bone allograft.

27. The material of claim 26, wherein the bone allograft is cancellous or cortical.

28. The material of claim 26, wherein the bone allograft is crushed, machined or whole.

29. A method according to claim 1, wherein contacting the radioprotectant-doped allograft with supercritical fluid is done at about 85 bar.

30. A method according to claim 1, wherein contacting the radioprotectant-doped allograft with a supercritical fluid is done for less than 24 hours.

31. A material for repairing a bone defect, the material comprising: a radioprotectant-doped allograft created by the method of claim 13.

32. A method according to claim 13, wherein contacting the radioprotectant-doped allograft with supercritical fluid is done at about 85 bar.

33. A method according to claim 13, wherein contacting the radioprotectant-doped allograft with a supercritical fluid is done for less than 24 hours.

34. The method according to claim 13, wherein the at least one additive is an antibiotic.

35. The method according to claim 13, wherein the at least one additive is an analgesic.

36. A method of making a radiation sterilized allograft, the method comprising:
   a. providing an allograft;
   b. cleaning the allograft;
   c. contacting the allograft with at least one radioprotectant (s), thereby obtaining a radioprotectant-doped allograft;
   d. contacting the radioprotectant-doped allograft with a supercritical fluid; thereby obtaining a homogenized radioprotectant doped allograft; and
   e. irradiating the homogenized radioprotectant doped allograft, thereby obtaining a radiation sterilized allograft,
   wherein the allograft is processed in whole form in the method.

37. A method of making a radiation sterilized allograft, the method comprising:

a. providing an allograft;
b. cleaning the allograft;
c. contacting the allograft with at least one radioprotectant(s), thereby obtaining a radioprotectant-doped allograft;
d. contacting the radioprotectant-doped allograft with a supercritical fluid;
thereby obtaining a homogenized radioprotectant doped allograft; and
e. irradiating the homogenized radioprotectant doped allograft, thereby obtaining a radiation sterilized allograft,
wherein the allograft is used without any further processing other than surface removal of tissue prior to incorporation of radioprotectant.

* * * * *

UNITED STATES PATENT AND TRADEMARK OFFICE
CERTIFICATE OF CORRECTION

PATENT NO. : 10,953,136 B2
APPLICATION NO. : 16/093540
DATED : March 23, 2021
INVENTOR(S) : Ebru Oral et al.

Page 1 of 1

It is certified that error appears in the above-identified patent and that said Letters Patent is hereby corrected as shown below:

In the Specification

Column 2, Line 67, "1500° C" should be --150° C--.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*